(12) United States Patent
Bowman et al.

(10) Patent No.: US 7,498,394 B2
(45) Date of Patent: Mar. 3, 2009

(54) (METH)ACRYLIC AND (METH)ACRYLAMIDE MONOMERS, POLYMERIZABLE COMPOSITIONS, AND POLYMERS OBTAINED

(75) Inventors: Christopher N. Bowman, Boulder, CO (US); Jeffrey W. Stansbury, Centennial, CO (US); Kathryn A. Berchtold, Los Alamos, NM (US); Jun Nie, Boulder, CO (US)

(73) Assignee: The Regents of the University of Colorado, Boulder, CO (US)

( * ) Notice: Subject to any disclaimer, the term of this patent is extended or adjusted under 35 U.S.C. 154(b) by 188 days.

(21) Appl. No.: 10/547,220

(22) PCT Filed: Feb. 20, 2004

(86) PCT No.: PCT/US2004/005124

§ 371 (c)(1),
(2), (4) Date: Aug. 22, 2005

(87) PCT Pub. No.: WO2004/077511

PCT Pub. Date: Sep. 10, 2004

(65) Prior Publication Data

US 2006/0252900 A1 Nov. 9, 2006

Related U.S. Application Data

(60) Provisional application No. 60/449,773, filed on Feb. 24, 2003, provisional application No. 60/456,868, filed on Mar. 21, 2003.

(51) Int. Cl.
*C08F 226/02* (2006.01)
*C08F 20/00* (2006.01)
*C07C 271/00* (2006.01)

(52) U.S. Cl. .................. 526/301; 526/302; 560/157; 560/158; 560/163

(58) Field of Classification Search .................. None
See application file for complete search history.

(56) References Cited

U.S. PATENT DOCUMENTS 5,064,921 A 11/1991 Blum et al.
5,331,073 A * 7/1994 Weinschenk et al. ........ 526/264
6,329,485 B1 * 12/2001 Vanderbilt ............... 526/318.1

FOREIGN PATENT DOCUMENTS

JP 2003-026735 * 1/2003

OTHER PUBLICATIONS

Sadoun et al., Makromeleculare Chemie, Synthesis and Characterization of Vinyl Monomers with Blocked Isocyanato Groups, 1987, vol. 188, pp. 1367-1373, p. 1368, top, compound 2b, p. 1373, lines 9-17.
International Search Report and Written Opinion of the International Searching Authority dated Jan. 4, 2005.
International Preliminary Report on Patentability from the International Bureau dated Sep. 9, 2005.

* cited by examiner

*Primary Examiner*—Paul A Zucker
(74) *Attorney, Agent, or Firm*—Merchant & Gould, P.C.

(57) ABSTRACT

The present invention provides novel (meth)acrylic and (meth)acrylamide monomers and polymers produced from those monomers. The monomers of the invention each include only a single vinyl functionality and at least one non-vinyl functionality that can be varied to achieve desired monomer/polymer properties. The invention additionally provides methods of producing polymers from these monovinyl monomers.

2 Claims, 14 Drawing Sheets

(METH)ACRYLIC AND (METH)ACRYLAMIDE MONOMERS, POLYMERIZABLE COMPOSITIONS, AND POLYMERS OBTAINED

CROSS-REFERENCES TO RELATED APPLICATIONS

This application is the national phase under 35 U.S.C. § 371 of International Application No. PCT/US2004/005124, which has an International filing date of Feb. 20, 2004 and which designated the United States of America, which claims the benefit of U.S. Provisional Application No. 60/449,773, filed Feb. 24, 2003, and U.S. Provisional Application No. 60/456,868, filed Mar. 21, 2003, the disclosures of which are incorporated by reference in their entirety for all purposes.

STATEMENT AS TO RIGHTS TO INVENTIONS MADE UNDER FEDERALLY SPONSORED RESEARCH AND DEVELOPMENT

This invention was made with government support under Grant Nos. DE10959 and EEC-0002971 awarded by the National Institutes of Health and the National Science Foundation, respectively. The government has certain rights in the invention.

COPYRIGHT NOTIFICATION

Pursuant to 37 C.F.R. §1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

BACKGROUND OF THE INVENTION

The photopolymerization or radiation-based curing of light sensitive materials is a multibillion dollar business. The photopolymer products of these processes are typically derived from polymers, oligomers, and/or monomers that can be selectively polymerized and/or crosslinked upon imagewise exposure to various types of electromagnetic radiation, including ultra-violet light, visible light, and electron beam radiation. Significant advantages that photopolymerizable systems have over other polymerization techniques, such as traditional thermal processing methods, include low energy requirements, spatial and temporal control of initiation, solvent-free formulations, and high polymerization rates at room temperature. They also provide tremendous chemical versatility in view of the wide range of monomers that can be photochemically polymerized.

Due to this unique set of advantages, photopolymerization systems have gained prominence for the solvent-free curing of polymer films as well as emerging applications in biomedical materials, conformal coatings, electronic and optical materials, and rapid prototyping of three dimensional objects. More specifically, photopolymers are made into different forms including films, sheets, liquids, and solutions, which are utilized in, e.g., printing plates, photoresists, stereolithography, and imaging. To further illustrate, photoresists are used to fabricate integrated circuits, flat panel displays, printed circuits, screen printing products, chemically milled parts, and micro- and nano-electromechanical systems (MEMS/NEMS). Liquid compositions can also be used for non-imaging applications such as adhesives, coatings, paints, inks, and related photosensitive products. Photopolymerizations also have in vivo applications in, e.g., open environments such as the oral cavity in addition to uses in invasive and minimally invasive surgery. In vivo photopolymerizations have even been performed transdermally.

Photopolymerization systems, processes, and related applications of radiation cured polymers are further described in a variety of general reference sources. Certain of these include, e.g., Lowe et al., *Test Methods for UV and EB Curable Systems*, Wiley—SITA Technology (1997), Drobny, *Radiation Technology for Polymers*, CRC Press (2002), Datta, *Rubber Curing Systems* (Rapra Review Report 144), Rapra (2002), Provder et al. (Eds.), *Film Formation in Coatings: Mechanisms, Properties, and Morphology* (ACS Symposium Series 790), American Chemical Society (2001), Mehnert et al., *Chemistry & Technology of UV & EB Formulation for Coatings, Inks & Paints, Vol. 1: UV & EB Curing Technology & Equipment*, Wiley—SITA Technology (1999), Neckers et al., *Chemistry & Technology of UV & EB Formulation for Coatings, Inks & Paints, Vol. 7: Photoinitiation for Polymerization: UV & EB at the Millenium*, Wiley—SITA Technology (1999), Satas et al. (Eds.), *Coatings Technology Handbook*, 2nd Ed., Marcel Dekker (2001), Bradley (ed.), *Chemistry & Technology of UV & EB Formulation, Vol. 3: Photoinitators for Free Radical Cationic & Anionic Photopolymerization*, 2nd Ed., Wiley—SITA Technology (1998), Warson et al., *Applications of Synthetic Resin Latices, Vol. 1: Fundamental Chemistry of Latices and Applications in Adhesives*, John Wiley & Sons (2001), Davidson, *Radiation Curing* (Rapra Review Report 136), Rapra (2001), and Fouassier, *Photoinitiated Polymerisation: Theory and Applications* (Rapra Review Report 100), Rapra (1997).

The quality and performance of polymers are linked to the cure characteristics of the polymerization system. Monomers that include multiple vinyl functionalities are an industry standard in many common photopolymerization schemes. Many of these multi-vinyl monomer-based polymerizations suffer from significant limitations. To illustrate, multi-vinyl monomers typically react to far less than quantitative double bond conversion. This generally results in polymeric materials having relatively high residual/leachable monomer content. Accordingly, these materials are often toxic and have limited durability. In addition to incomplete reactions, multivinyl monomer-based polymerizations are typically slow, requiring lengthy exposure times at high radiation intensities. These aspects increase production costs and generally have negative environmental implications.

In view of the foregoing discussion, it is apparent that there is a substantial need for monomers that have higher polymerization rates and that polymerize more completely than conventional monomers with multiple vinyl functionalities. For example, improvements in monomer curing efficiency would allow optimum polymer properties to be achieved with minimized irradiation times and intensities. These and a variety of other features of the present invention will become apparent upon complete review of the following disclosure.

SUMMARY OF THE INVENTION

The present invention generally relates to polymer chemistry. More specifically, the invention provides novel (meth) acrylic and (meth)acrylamide monomers that each include only a single vinyl polymerizable moiety or functionality. The monomers disclosed herein generally have high polymerization reactivities that in many cases exceed the rates of reaction typically achieved in homopolymerizations involving monomers having multiple vinyl functionalities. Accordingly, the present invention also provides polymerizable compositions that typically include selected combinations of the novel (meth)acrylic and (meth)acrylamide monomers disclosed herein. Optionally, a polymerizable composition of the invention includes at least one of the novel monomers disclosed herein in addition to other monomers, such as those comprising multiple vinyl functionalities. Further, the invention additionally relates to the polymers produced from these novel monomers and to the unique material properties or characteristics of these polymers, which properties are typically readily tailored to suit varied specifications.

In one aspect, the invention provides a monomer corresponding to a compound of formula (I):

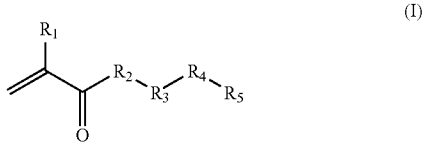

in which $R_1$ is $CH_3$ or H, $R_2$ is O or NH, and $R_3$ is $(CH_2)_n$ or $[(CH_2)_nO]_m$, where n and m are integers independently selected from 1 to 50 inclusive. $R_4$ is $(R_{4a})_g Y_e (R_{4b})_f Z_q$ in which $R_{4a}$ and $R_{4b}$ are independently selected from carbonates, carbamates, ureas, thiocarbonates, dithiocarbonates, trithiocarbonates, thiocarbamates, dithiocarbamates, and thioureas. Further, g and f are independently 0 or 1, Y is $CH_2$ or $(CH_2)_pO$, e and q are integers independently selected from 0 to 50 inclusive, Z is $CH_2$ or $(CH_2)_sO$, and p and s are integers independently selected from 1 to 50 inclusive. $R_5$ is a substituted or unsubstituted cyclic end group. In addition, (a) if $R_2$ is O, n is an integer from 2 to 6 inclusive, m is 1, $R_{4a}$ is a carbonate, Y is $CH_2$, e is an integer from 1 to 6 inclusive, and f and q are 0, then $R_5$ is a non-vinyl cyclic substituent other than a five-membered cyclic carbonate; (b) if $R_2$ is O, $R_3$ is $(CH_2)_n$, n is 2, $R_{4a}$ is a carbamate, Y is $CH_2$, e is 1, f and q are 0, and the carbamate of $R_{4a}$ comprises an O attached to Y, then $R_5$ is a non-vinyl cyclic substituent other than a five-membered cyclic carbonate; (c) if $R_2$ is O, $R_3$ is $(CH_2)_n$, n is an integer from 2 to 6 inclusive, $R_{4a}$ is a carbamate, e, f, and q are 0, and the carbamate of $R_{4a}$ comprises an N attached to $R_5$, then $R_5$ is a non-vinyl cyclic substituent other than a cyclohexyl or a $C_{6-8}$ aryl; (d) if $R_2$ is O, n is an integer from 2 to 12 inclusive, $R_{4a}$ is a carbamate, e, f, and q are 0, and the carbamate of $R_{4a}$ comprises an O attached to $R_5$, then $R_5$ is a non-vinyl cyclic substituent other than a phenyl that is unsubstituted or substituted by $C_1$-$C_4$ alkyl, $C_1$-$C_4$ alkoxy or by a halogen; (e) if $R_2$ is O, n is an integer from 2 to 6 inclusive, m is 0, $R_{4a}$ is a carbonate, and e, f, and q are 0, then $R_5$ is a non-vinyl cyclic substituent other than a substituted or unsubstituted $C_{5-12}$ cycloalkyl or a substituted or unsubstituted phenyl; and (f) if $R_2$ is O, and g, e, f, and q are 0, then $R_5$ is a non-vinyl cyclic substituent other than a five-membered cyclic carbonate or a five-membered cyclic carbamate having an N attached to $R_3$. In preferred embodiments, the monomer is selected from Table I.

The cyclic end group of $R_5$ typically includes a ring having 3, 4, 5, 6, 7, 8, or more members. For example, the cyclic end group of $R_5$ optionally comprises one or more of, e.g., an aromatic group, a cyclic carbonate, a cyclic carbamate, a cyclic urea, a cyclic thiocarbonate, a cyclic dithiocarbonate, a cyclic trithiocarbonate, a cyclic thiocarbamate, a cyclic dithiocarbamate, a cyclic thiourea, or the like.

In other aspects, the invention provides a polymerizable composition that includes at least two monomers in which at least one of the monomers corresponds to the compound of formula (I) described above. The polymerizable composition, which is typically in the liquid state, optionally further includes at least one diluent, at least one initiator, at least one additive, and/or the like. The invention also provides a polymer comprising at least one monomeric unit derived from the compound of formula (I) described above. In addition, the invention also relates to an article comprising the polymers described herein. For example, the article optionally includes at least one coating that comprises a polymer described herein. To further illustrate, the article is optionally selected from, e.g., a dental restorative material, a lithographic material, a membrane, an adhesive, a printing plate, an ink, a holographic material, a biomaterial, and the like.

In an additional aspect, the invention provides a method of producing a polymer. The method includes reacting at least two monomers with one another in which at least one of the monomers corresponds to a compound of formula (I), as described above. The reacting step includes one or more of, e.g., irradiating a composition comprising the monomers, heating a composition comprising the monomers, adding at least one catalyst to a composition comprising the monomers, etc. In some embodiments, a composition that includes the monomers further comprises, e.g., at least one initiator. The monomers typically react with one another to substantially quantitative double bond conversion.

The polymerizations were performed at 25° C. with an initiator concentration of 0.1 wt % and a light intensity of 5 $mW/cm^2$.

Figure 8:
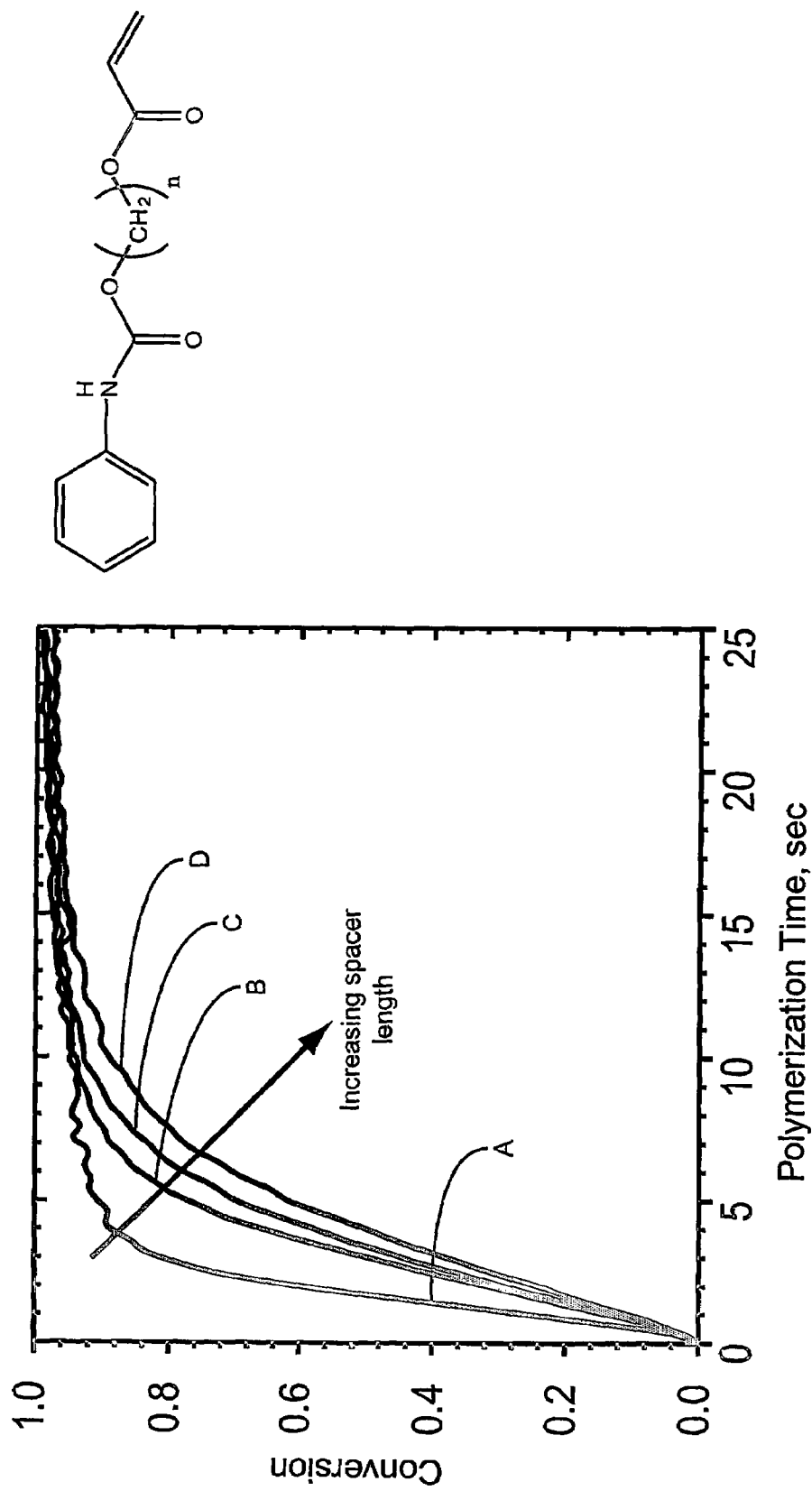

FIG. 8 is a data graph (abscissa—polymerization time (seconds); ordinate—extent of conversion) that shows the impact of phenyl carbamate acrylate spacer length ($R_3$) on reactivity. The polymerizations were performed at 67° C. with an initiator concentration of 0.1 wt % and a light intensity of 5 $mW/cm^2$.

Figure 9:
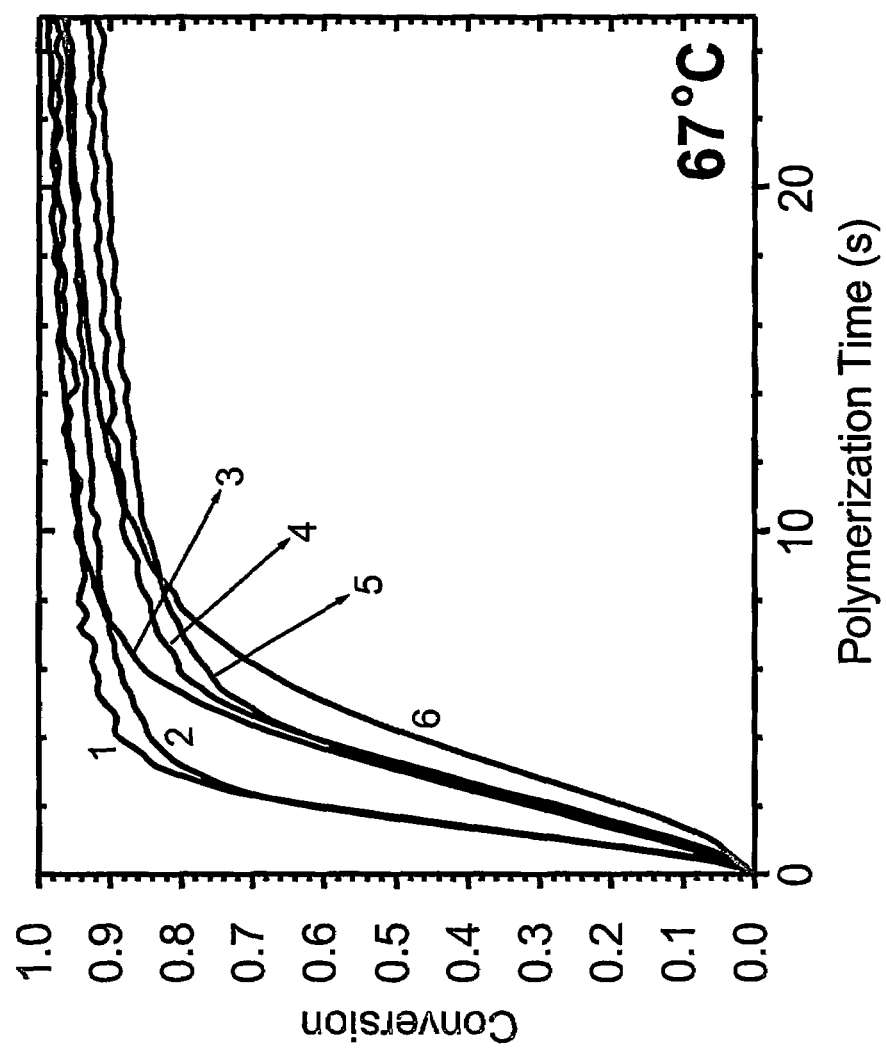

FIG. 9 is a data graph (abscissa—polymerization time (seconds); ordinate—extent of conversion) that shows the steady state bulk polymerizations of the 5 electron withdrawing (fluoro-substituted) PNCOA monomers. The monovinyl systems presented contain: (1) unsubstituted, (2) meta, (3) ortho, (4) para, (5) penta, and (6) dimeta fluoro-substituted phenyl $R_5$ substituents. Polymerizations were conducted at 67° C. with 0.1 wt % DMPA at $5mW/cm^2$.

Figure 10:
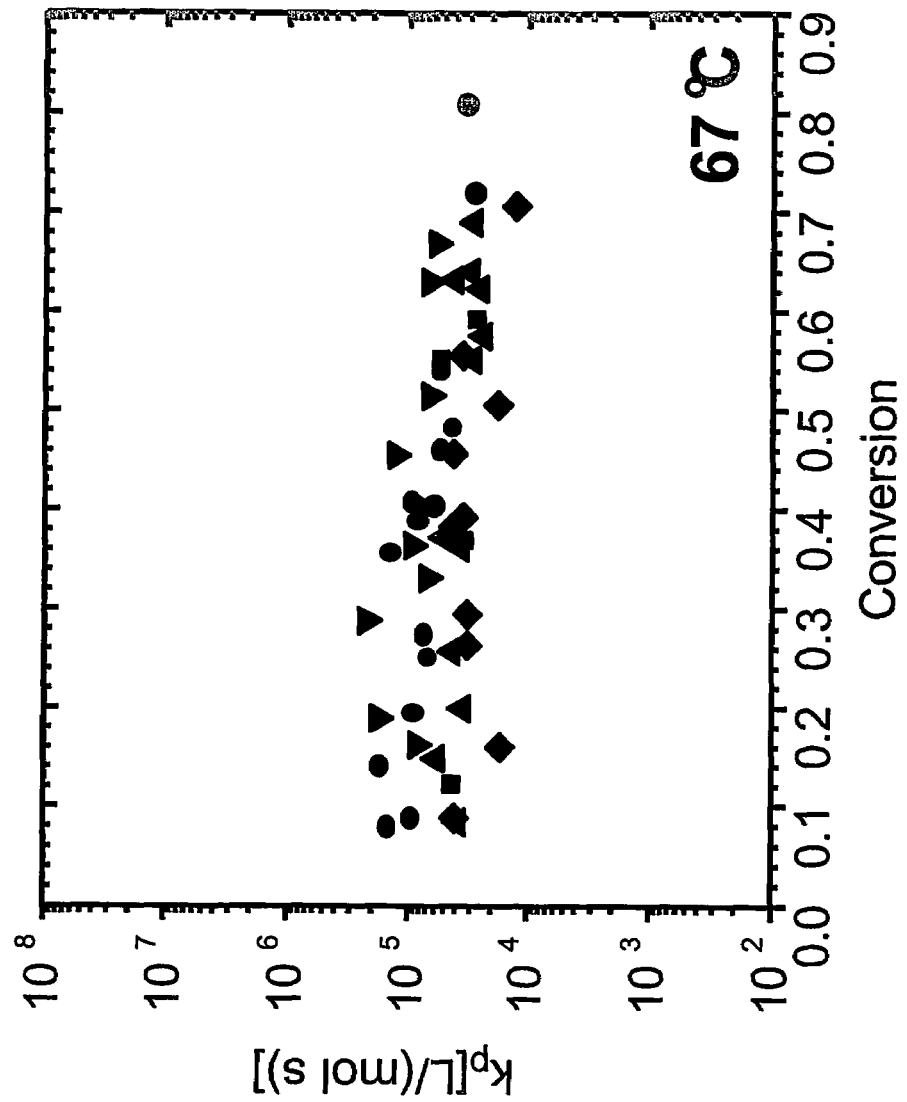

FIG. 10 is a data graph that illustrates the propagation kinetic constant ($k_p$)(ordinate) versus conversion (abscissa) for fluoro-substituted PNCOA monomers. The monovinyl systems presented contain: (■) Unsubstituted, (●) para, (▲) meta, (▼) ortho, and (♦) penta fluoro-substituted phenyl $R_5$ substituents. The polymerizations were performed at 67° C. with an initiator concentration of 0.1 wt % and a light intensity of 5 $mW/cm^2$.

Figure 11:
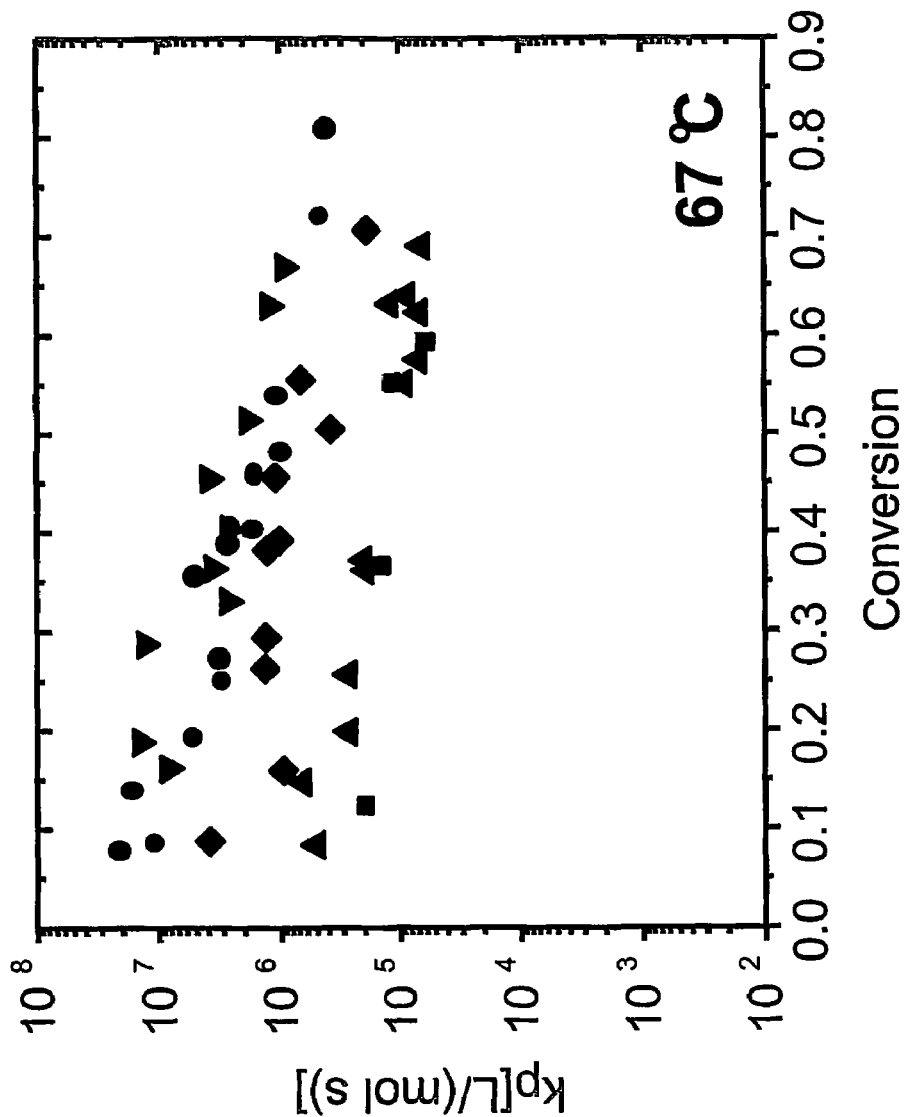

FIG. 11 is a data graph that illustrates the termination kinetic constant ($k_t$)(ordinate) versus conversion (abscissa) for fluoro-substituted PNCOA monomers. The monovinyl systems presented contain: (■) Unsubstituted, (●) para, (▲) meta, (▼) ortho, and (♦) penta fluoro-substituted phenyl $R_5$ substituents. The polymerizations were performed at 67° C. with an initiator concentration of 0.1 wt % and a light intensity of 5 $mW/cm^2$.

Figure 12:
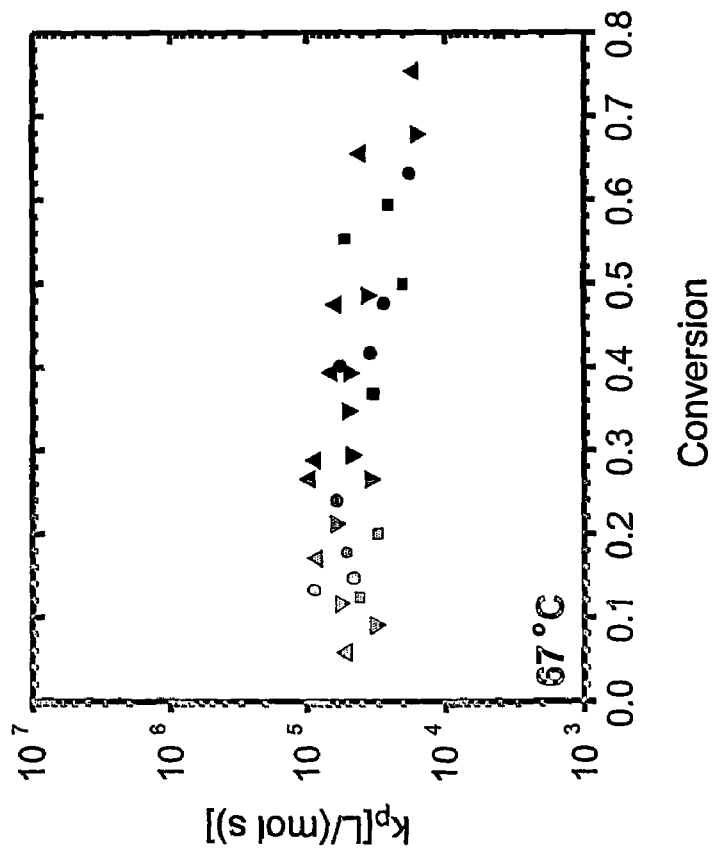

FIG. 12 is a data graph that illustrates the propagation kinetic constant ($k_p$)(ordinate) versus conversion (abscissa) for a methoxy-substituted PNCOA monomer. The monovinyl systems presented contain: (■) Unsubstituted, (●) para, (▲) meta, and (▼) ortho methoxy-substituted phenyl $R_5$ substituents. The polymerizations were performed at 67° C. with an initiator concentration of 0.1 wt % and a light intensity of 5 $mW/cm^2$.

Figure 13:
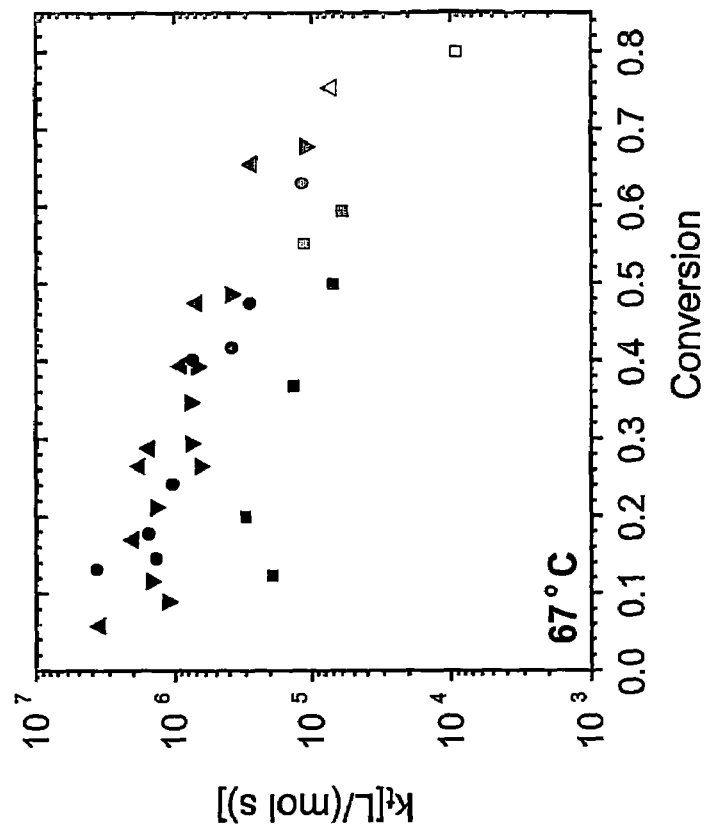

FIG. 13 is a data graph that illustrates the termination kinetic constant ($k_t$)(ordinate) versus conversion (abscissa) for a methoxy-substituted PNCOA monomer. The monovinyl systems presented contain: (▦) Unsubstituted, (○) para, (△) meta, and (▽) ortho methoxy-substituted phenyl $R_5$ substituents. The polymerizations were performed at 67° C. with an initiator concentration of 0.1 wt % and a light intensity of 5 $mW/cm^2$.

Figure 14:
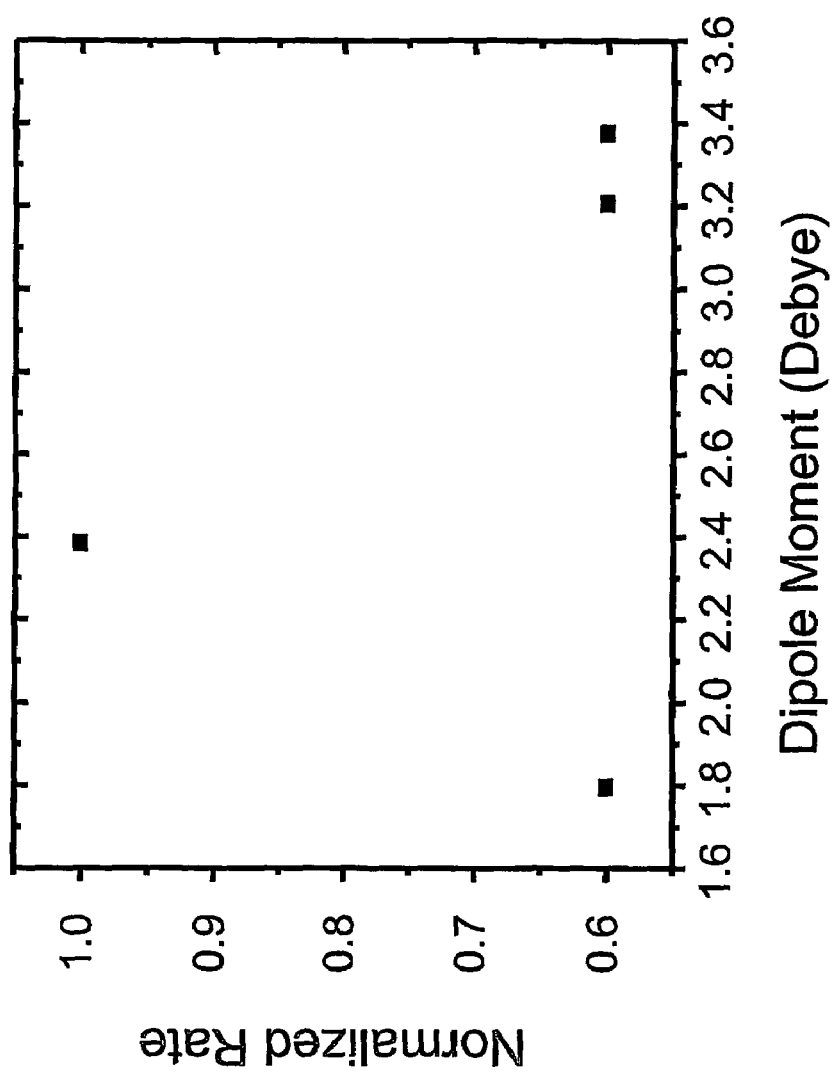

FIG. 14 is a data graph that shows normalized reaction rate (ordinate) versus dipole moment (Debye)(abscissa) for various methoxy substituted acrylate monomers.

Figure 15:
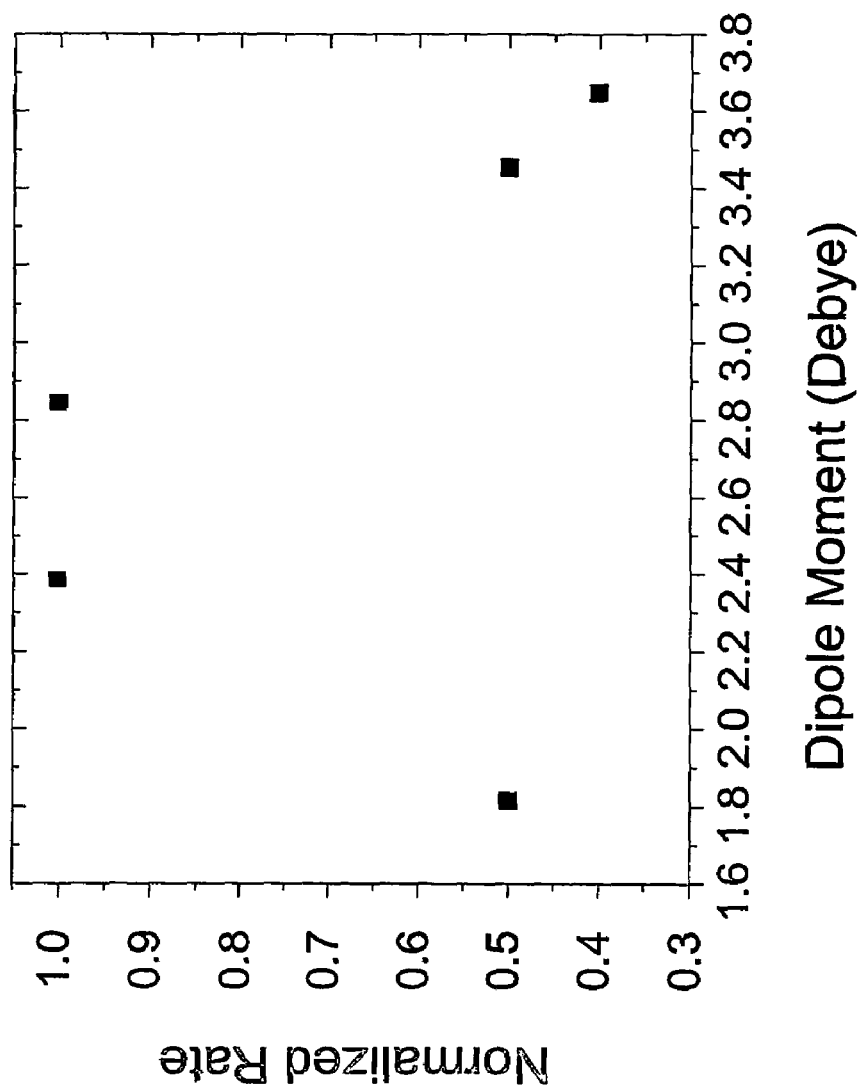

FIG. 15 is a data graph that shows normalized reaction rate (ordinate) versus dipole moment (Debye)(abscissa) for various fluoro substituted acrylate monomers.

DETAILED DISCUSSION OF THE INVENTION

I. Definitions

As used herein, the terms set forth with particularity below and grammatical variations used herein have the following definitions. If not otherwise defined, all terms used herein have the meaning commonly understood by a person skilled in the art to which this invention pertains.

A "functionality" refers to a group of atoms that represents a potential reaction site in an organic compound. For example, a monomer of the present invention includes a single vinyl functionality (i.e., a single univalent $CH_2=CH$ group) and at least one non-vinyl functionality (e.g., a secondary functionality, a tertiary functionality, and/or the like). Non-vinyl functionalities ($R_4$) are secondary, tertiary, etc. to the vinyl functionality of the monomers described herein. A mono-vinyl monomer of the invention also includes a cyclic end group as $R_5$ that is optionally also a functionality. In certain embodiments of the invention, polymers produced from the monomers described herein are cross-linked or branched, e.g., via labile hydrogens and/or active sites associated with $R_3$, via the non-vinyl groups of $R_4$ and/or $R_5$, etc.

A "moiety" refers to one of the portions into which a molecule is divided (e.g., a functional group, substituent group, or the like). For example, a monomer of the present invention includes a single vinyl moiety.

A "polymer" refers to a compound that includes two or more monomeric units. A polymer of the present invention includes at least one monomeric unit derived (e.g., through a chemical modification, such as a polymerization reaction, etc.) from a monomer described herein.

The phrases "aryl group" and "aromatic group" are used interchangeably herein to refer to a substituent group of atoms or moiety that is derived from an aromatic system. Exemplary aryl groups that are optionally included in the monomers of the present invention include, e.g., phenyl groups, benzyl groups, tolyl groups, xylyl groups, or the like. Aryl groups optionally include multiple aromatic rings (e.g., diphenyl groups, etc.). In addition, an aryl group can be substituted or unsubstituted.

The term "substantially quantitative double bond conversion" refers to a polymerization reaction in which greater than 50% by weight of the monomers in the reaction mixture or composition are converted to polymer. In a reaction that includes the monomers of the invention, for example, typically more than 75% of the monomers in the reaction mixture are converted to polymer, more typically greater 85% of the monomers in the reaction mixture are converted to polymer, and still more typically greater 95% of the monomers in the reaction mixture are converted to polymer.

The term "reactivity" is defined as the maximum polymerization rate normalized by the initial monomer concentration in a given polymerization reaction.

II. Mono-vinyl Photopolymerization Systems

The present invention relates to novel acrylate, acrylamide, methacrylate and methacrylamide monomers bearing secondary and in some cases tertiary, non-vinyl functionalities and varied end group substituents, their high polymerization reactivity, and the unique material properties of the polymers that they form. The monomers of the invention are mono-vinyl, including only single reactive double bonds. The relative placement, orientation, chemistry, and electronic characteristics of the non-vinyl functionalities and end group substituents designed into these novel materials leads to extremely rapid polymerizations and versatile combinations of material properties. Although the monomers of the invention each include only a single vinyl polymerizable moiety, they form complex crosslinked (3-D), insoluble, polymer networks (e.g., rubbery polymer networks, glassy polymer networks, etc.) on time scales that rival those of the industry standard, multi-vinyl containing monomers. Examples that illustrate the reactivity of the monomers of the present invention in comparison to certain multi-vinyl monomers and other aspects of the invention are provided below.

Additionally, in contrast to their multi-vinyl counterparts, the monomers described herein typically react to substantially quantitative double bond conversion. This feature translates into materials with low residual/leachable monomer content, and thus, lower toxicity and a higher resistance to material property changes over time, i.e., an increase in the lifetime or durability of the material. The rapid and relatively complete polymerization of these novel monomers also translates into minimal required exposure times and intensities, traits that have significance for a wide range of curing applications, e.g., filled and multi-layer polymerizations, in addition to beneficial economic implications, including reduced production costs. This decrease in exposure time and initiation intensity has significance for a wide range of curing applications. Some examples include applications that require cure through a secondary layer, cure of systems containing fillers, which absorb a fraction of the initiating light, and applications that prohibit the use of an inert atmosphere for cure, e.g., in vivo applications. In addition, the physical characteristics, i.e., physical state (solid, liquid), viscosity, refractive index, and absorptivity, of these monomers can also be readily manipulated and tailored for a specific application via subtle changes to the structure and chemistry. Furthermore, in certain embodiments, initiator concentrations used in the polymerization reactions can be reduced relative to more conventional protocols without compromising the rate or extent of cure. This reduction positively impacts on the long-term color stability of some polymer products, as initiators are a leading cause of polymer discoloration and long-term degradation reactions. Additional details relating to all aspects of the present invention are provided in, e.g., Kathryn Ann Berchtold, *Impact of Monomer Structure and Termination Kinetics on Free Radical Photopolymerizations*, Ph.D. Thesis, Department of Chemical Engineering, University of Colorado, November 2001, which is incorporated by reference in its entirety for all purposes.

In particular, the mono-vinyl monomers of the invention correspond to a compound of the general formula (I):

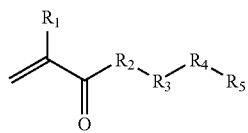

in which $R_1$ is $CH_3$ or H, $R_2$ is O or NH, and $R_3$ is $(CH_2)_n$ or $[(CH_2)_nO]_m$, where n and m are integers independently selected from 1 to 50 inclusive. $R_4$ is $(R_{4a})_g Y_e (R_{4b})_f Z_q$ in which $R_{4a}$ and $R_{4b}$ are independently selected from carbonates, carbamates, ureas, thiocarbonates, dithiocarbonates, trithiocarbonates, thiocarbamates, dithiocarbamates, and thioureas. Further, g and f are independently 0 or 1, Y is $CH_2$ or $(CH_2)_pO$, e and q are integers independently selected from 0 to 50 inclusive, Z is $CH_2$ or $(CH_2)_sO$, and p and s are integers independently selected from 1 to 50 inclusive.

To further illustrate, preferred non-vinyl functionalities ($R_4$) include those of formulae:

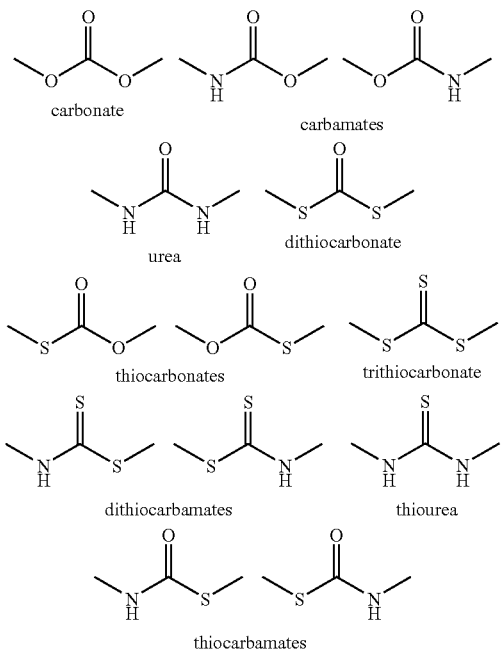

In the mono-vinyl monomers of the present invention, $R_5$ is a substituted or unsubstituted cyclic end group. The cyclic end group of $R_5$ typically includes a ring having 3, 4, 5, 6, 7, 8, or more members. In preferred embodiments, for example, $R_5$ comprises one or more of, e.g., an aromatic group, a cyclic carbonate, a cyclic carbamate, a cyclic urea, a cyclic thiocarbonate, a cyclic dithiocarbonate, a cyclic trithiocarbonate, a cyclic thiocarbamate, a cyclic dithiocarbamate, a cyclic thiourea, or the like. In addition, in a mono-vinyl monomer of the invention:

(a) if $R_2$ is O, n is an integer from 2 to 6 inclusive, m is 1, $R_{4a}$ is a carbonate, Y is $CH_2$, e is an integer from 1 to 6 inclusive, and f and q are 0, then $R_5$ is a non-vinyl cyclic substituent other than a five-membered cyclic carbonate;

(b) if $R_2$ is O, $R_3$ is $(CH_2)_n$, n is 2, $R_{4a}$ is a carbamate, Y is $CH_2$, e is 1, f and q are 0, and the carbamate of $R_{4a}$ comprises an O attached to Y, then $R_5$ is a non-vinyl cyclic substituent other than a five-membered cyclic carbonate;

(c) if $R_2$ is O, $R_3$ is $(CH_2)_n$, n is an integer from 2 to 6 inclusive, $R_{4a}$ is a carbamate, e, f, and q are 0, and the carbamate of $R_{4a}$ comprises an N attached to $R_5$, then $R_5$ is a non-vinyl cyclic substituent other than a cyclohexyl or a $C_{6-8}$ aryl;

(d) if $R_2$ is O, n is an integer from 2 to 12 inclusive, $R_{4a}$ is a carbamate, e, f, and q are 0, and the carbamate of $R_{4a}$ comprises an O attached to $R_5$, then $R_5$ is a non-vinyl cyclic substituent other than a phenyl that is unsubstituted or substituted by $C_1$-$C_4$ alkyl, $C_1$-$C_4$ alkoxy or by a halogen;

(e) if $R_2$ is O, n is an integer from 2 to 6 inclusive, m is 0, $R_{4a}$ is a carbonate, and e, f, and q are 0, then $R_5$ is a non-vinyl cyclic substituent other than a substituted or unsubstituted $C_{5-12}$ cycloalkyl or a substituted or unsubstituted phenyl; and (f) if $R_2$ is O, and g, e, f, and q are 0, then $R_5$ is a non-vinyl cyclic substituent other than a five-membered cyclic carbonate or a five-membered cyclic carbamate having an N attached to $R_3$.

The structures of certain representative preferred monomers of the present invention are provided in Table I. Specific exemplary monomer structures that are included in this invention are presented, referred to, and/or described in this table. Only certain acrylate structures are illustrated, but for each monomer, the corresponding acrylamide, methacrylate, and methacrylamide monomers are also claimed herein. Also, only the case where an alkyl spacer group ($R_3$) corresponding to the $(CH_2)_2$ is shown; other alkyl and alkyl glycol spacer groups, i.e., $(CH_2)_n$ or $[(CH_2)_nO]_m$, are also optionally included where n and m are independently selected from integers from 1-50 inclusive. Structures having alkyl or alkyl glycol spacer groups disposed at Y and/or Z, in a compound of formula (I) are also included. Further, only the non-sulfur containing non-vinyl functionalities ($R_4$) are illustrated (i.e., carbonates, carbamates, and ureas), but those containing sulfur (i.e., dithiocarbonate, dithiocarbamate, thiocarbonate, thiourea, trithiocarbontate, and thiocarbamate structures shown above) are also claimed herein. Monomers with single non-vinyl functionalities ($R_{4a}$ or $R_{4b}$) and those with multiple non-vinyl functionalities ($R_{4a}$ or $R_{4b}$) in any combination (i.e., the same or different functionalities) are also claimed herein. Additionally, only exemplary 5 and 6 membered cyclic carbonate ring structures and certain 6 membered aromatic groups (i.e., phenyl and diphenyl groups) are illustrated below at $R_5$. Other ring structures that include, e.g., 3, 4, 7, 8 or more members are also claimed. In addition to the cyclic carbonates at $R_5$, cyclic ureas, cyclic carbamates, cyclic dithiocarbonates, cyclic dithiocarbamates, cyclic thiocarbonates, cyclic thioureas, cyclic trithiocarbonates, and cyclic thiocarbamates are also included at $R_5$. The specific exemplary monomer structures are as follows:

TABLE I

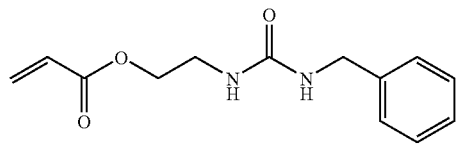

Compound 1

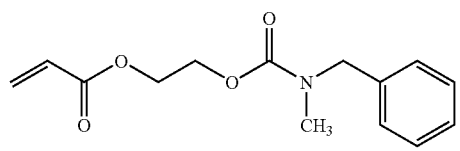

Compound 2

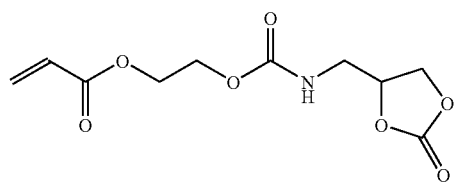

Compound 3

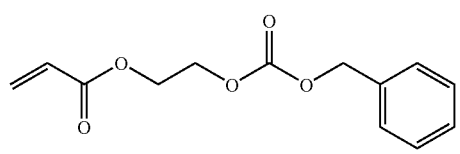

Compound 4

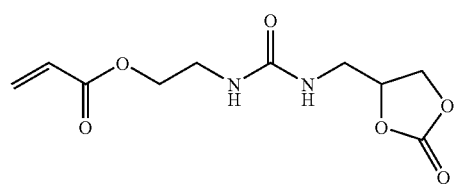

Compound 5

TABLE I-continued
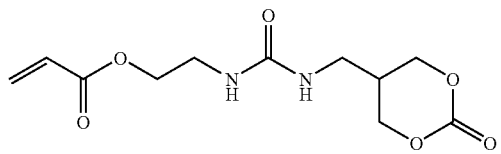
Compound 6
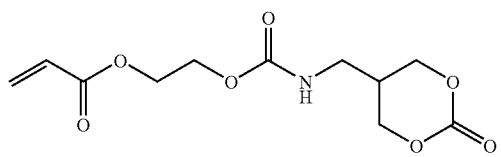
Compound 7
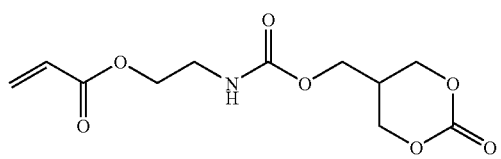
Compound 8
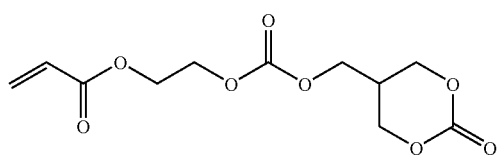
Compound 9
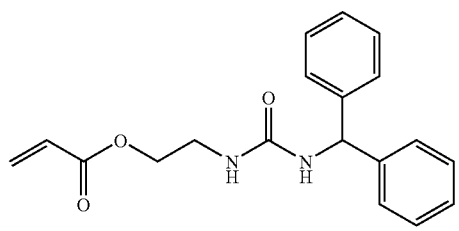
Compound 10
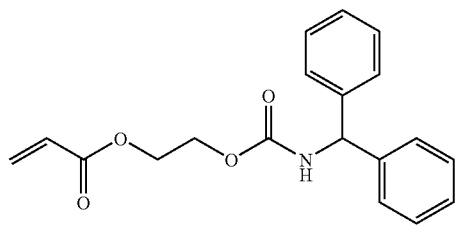
Compound 11
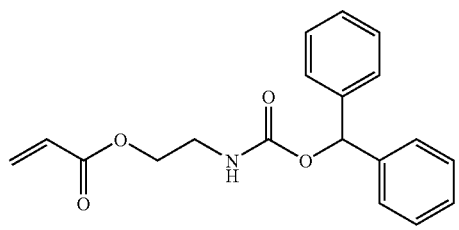
Compound 12

TABLE I-continued
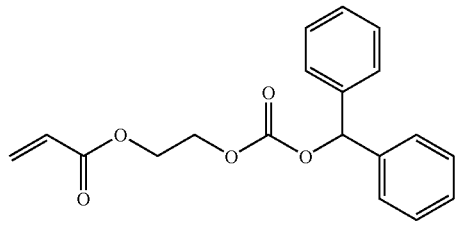
Compound 13
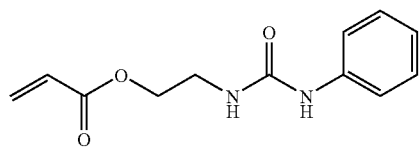
Compound 14
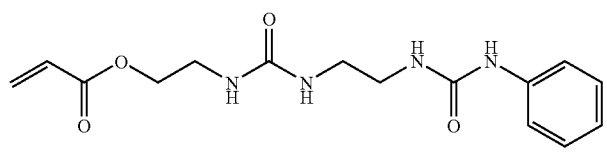
Compound 15
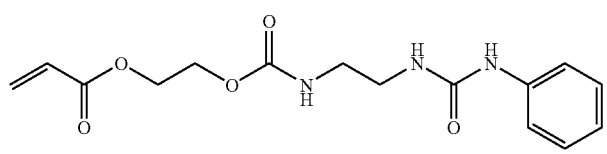
Compound 16
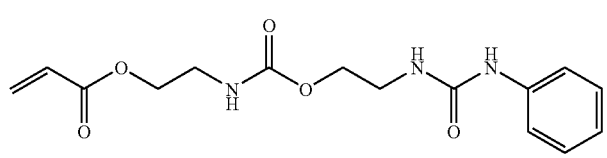
Compound 17
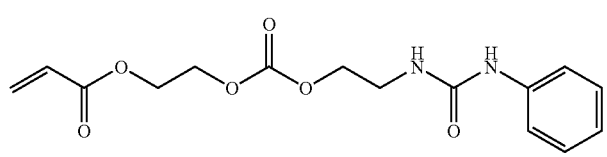
Compound 18
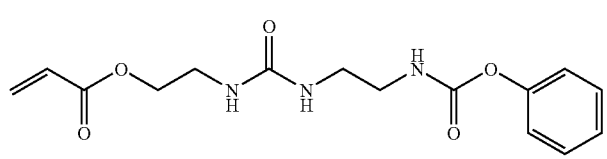
Compound 19

TABLE I-continued
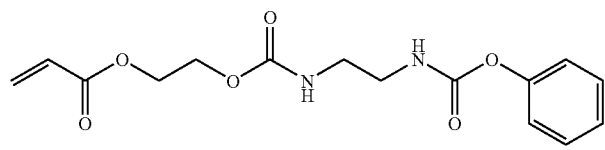
Compound 20
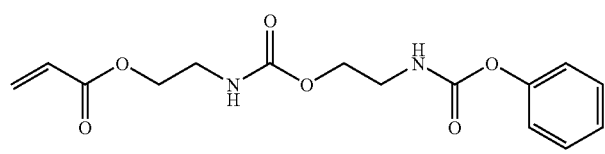
Compound 21
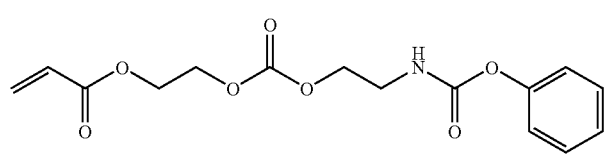
Compound 22
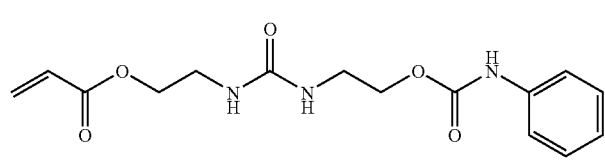
Compound 23
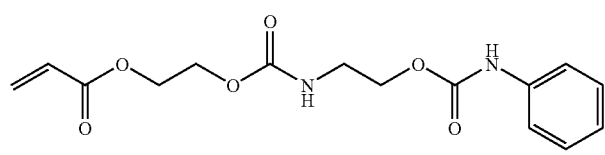
Compound 24
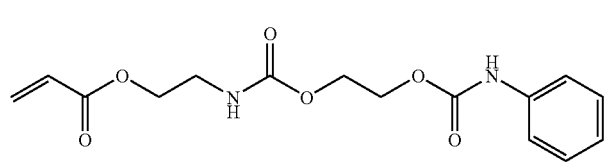
Compound 25
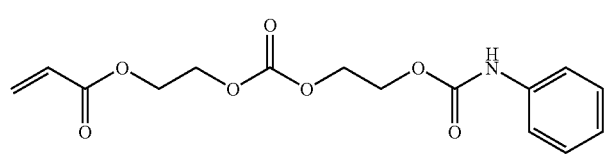
Compound 26
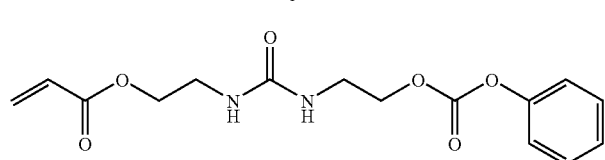
Compound 27

TABLE I-continued

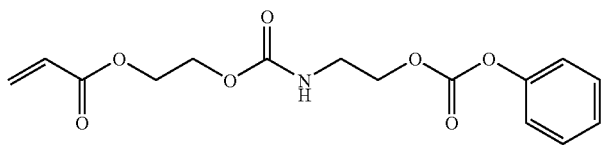

Compound 28

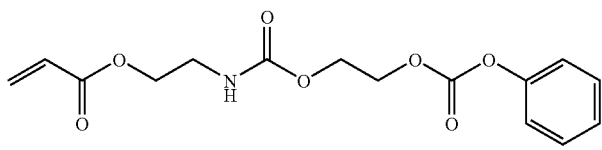

Compound 29

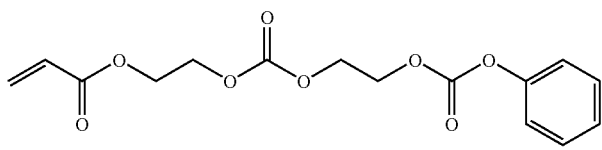

Compound 30

The synthesis and purification of the mono-vinyl monomers of the invention are described in further detail in the examples provided below. Various synthetic techniques that can be adapted for use in the monomer synthesis protocols and polymerization reactions of the present invention are generally known and described in, e.g., March, *Advanced Organic Chemistry: Reactions, Mechanisms, and Structure*, 4$^{th}$ Ed., John Wiley & Sons, Inc. (1992), Carey and Sundberg, *Advanced Organic Chemistry Part A: Structure and Mechanism*, 4th Ed., Plenum Press (2000), and in the references provided therein. Chemical starting materials and other reaction components useful in the synthesis of the monomers of the present invention are readily available from various commercial suppliers including, e.g., Sigma-Aldrich, Inc. From the examples provided herein and the general knowledge in the art it will be apparent to one of skill how to synthesize and purify the monomers of the present invention.

The polymers of the invention are produced by reacting at least two monomers with one another in which at least one of the monomers corresponds to a compound of the general formula (I), described above. For example, polymerizable compositions (e.g., radiation curable compositions, etc.) of the invention optionally include only a single type of monomer, e.g., when a homopolymer is sought. When a copolymer is desired, compositions typically include two or more different mono-vinyl monomers of the invention. See, e.g., Table I, above. However, these compositions also optionally comprise other types of monomers including multi-vinyl monomers, such as hexanediol diacrylate, 1,6 hexanediol dimethacrylate, or the like. To further illustrate, a composition optionally comprises a mono-vinyl monomer of the invention, such as cyclic carbonate urea methacrylate, etc. and a multi-vinyl monomer, such as hexanediol diacrylate. In addition, the compositions of the present invention optionally include monomers having other radiation curable functional groups, such as vinylether, fumarate, maleate, oxolane, epoxy, itaconate, and/or other groups. The proportions of the constituent monomers in a composition may also vary according to the mechanical properties desired for the polymer. In certain embodiments, for example, a composition of the invention includes at least one monomer described herein in an amount of at least about 1% by weight of the total amount of components in the composition, preferably at least about 5% by weight, more preferably at least about 10% by weight, even more preferably at least about 15% by weight and still more preferably at least about 25% by weight (e.g., at least about 35%, 45%, 55%, 65%, 75%, or more by weight of the total amount of components in the composition).

As mentioned, the polymerizable compositions used in these processes are typically varied according to the desired material properties (e.g., strength (e.g., elongation strength, tensile strength, etc.), hardness (e.g., pendulum hardness), flexibility, insolubility, etc.) sought in the polymer product. The particular mono-vinyl (meth)acrylic and (meth)acrylamide monomers included in a given composition can include any of the non-vinyl functionalities ($R_4$) described herein or essentially any combination of those functionalities in monomers that comprise multiple non-vinyl functionalities ($R_4$). To illustrate, non-vinyl functionalities are optionally selected according to the type of cross-linking desired in the polymer product.

In addition, polymerizable compositions are further varied based upon the cyclic end groups ($R_5$) included in the composition. As described above, these end groups optionally include cyclic non-vinyl functionalities (e.g., cyclic carbonate, cyclic carbamate, cyclic urea, etc.) including those with sulfur substitutions. In certain embodiments, cyclic end groups ($R_5$) include one or more aromatic groups (e.g., benzyl, phenyl, diphenyl, or other groups).

Monomers are further varied by including alkyl spacer groups (e.g., $(CH_2)_n$) of selected lengths. For example, n is typically an integer from 1 to 50 inclusive, more typically an integer from 1 to 25 inclusive, and still more typically integer from 1 to 10 inclusive (e.g., 2, 3, 4, 5, 6, 7, 8, or 9). In some embodiments, spacer groups are alkyl glycol groups (e.g., $[(CH_2)_nO]_m$). In these embodiments, n and m are also typically integers independently selected from 1 to 50 inclusive, more typically integers independently selected from 1 to 25 inclusive, and still more typically integers independently selected from 1 to 10 inclusive (e.g., 2, 3, 4, 5, 6, 7, 8, or 9). Additional details relating to the particular monomers selected for inclusion in a given composition are described above and in the examples provided below.

In some embodiments, compositions of the invention further include quantities (e.g., a few % by weight) of photo-crosslinking or photo-polymerization initiators, solvents/diluents (e.g., reactive and/or non-reactive diluents), photosensitizers/synergists (e.g., diethylamine, triethylamine, ethanolamine, ethyl 4-dimethylaminobenzoate, 4-dimethylaminobenzoic acid, and the like), and/or additives typically utilized in polymerizable compositions. Exemplary initiators which are optionally utilized include benzoin ethers and phenone derivatives such as benzophenone or diethoxyacetophenone, either by themselves or in combination with a tertiary amine, e.g., methyldiethanolamine, etc. More specific exemplary photo-polymerization initiators include, e.g., 3-methylacetophenone, xanthone, fluorenone, fluorene, 2-hydroxy-2-methyl-1-phenylpropan-1-one, triphenylamine, thioxanethone, diethylthioxanthone, 2,2-dimethoxy-2-phenylacetophenone, benzyl methyl ketal, 2,4,6-trimethylbenzoyldiphenylphosphine, and the like. Other initiators that are also optionally utilized are generally known in the art to which this invention pertains. Mixtures of initiators are also optionally utilized. Photo-polymerization initiators are available from a variety of commercial suppliers including, e.g., Ashland, Inc., UCB, BASF, Ciba Specialty Chemicals Co., Ltd., etc. Although compositions having higher initiator contents are optionally utilized, compositions with a low initiator content (e.g., 1 wt % or less), or containing no initiator, are typically preferred. Compositions with lower levels of an initiator are typically more transparent to UV or other forms of electromagnetic radiation, which makes it possible to polymerize in greater depths, e.g., in thicknesses of 1 cm or more.

Polymerizable compositions (e.g., coating compositions, etc.) utilized to produce the polymers of the present invention may also contain essentially any additive that is typically utilized in these process, such as agents for adjusting the surface gloss of the polymer, surfactants, fillers, colorants, antioxidants, UV absorbers, heat polymerization inhibitors, light stabilizers, silane coupling agents, coating surface improvers, leveling agents, preservatives, plasticizers, lubricants, solvents, aging preventives, and the like. In certain embodiments, amine compounds (e.g., diethylamine, diisopropylamine, diallylamine, etc.) can be added to polymerizable composition to prevent the generation of hydrogen gas. These and other additives are generally known in the art and readily available from many different commercial sources, such as UCB, Ashland, Inc., Sigma-Aldrich, Inc., BASF, Ciba Specialty Chemicals Co., Ltd., Sankyo Co., Ltd., Sumitomo Chemical Industries Co., Ltd., Shin-Etsu Chemical Co, Ltd., and the like.

The polymerization reactions of the invention are performed under varied conditions. For example, the reacting step optionally includes one or more of, e.g., irradiating a composition comprising the monomers, heating a composition comprising the monomers, adding at least one catalyst to a composition comprising the monomers, and/or the like. The radiation utilized may be, for example, electromagnetic radiation, electron bombardment, or nuclear radiation. In certain embodiments, for example, an article or other substrate coated with a polymerizable composition described herein is exposed to the radiation source (e.g., a UV or electron beam radiation source), for a selected period of time. To further illustrate, one photon and/or two photon polymerizations are optionally utilized. Additional details relating to single and multiple photon polymerizations are provided in, e.g., Macak et al. (2000) "Electronic and vibronic contributions to two-photon absorption of molecules with multi-branched structures," *J. Chem. Phys.* 113(17):7062, Luo et al. (2000) "Solvent induced two-photon absorption of push-pull molecules," *J. Phys. Chem.* 104:4718, and Luo et al. (1994) "One- and two-photon absorption spectra of short conjugated polyenes," *J. Phys. Chem.* 98:7782. The intensity of light utilized to polymerize the monomers of the invention is typically between about 1 and about 50 $mW/cm^2$, more typically between about 1 and about 25 $mW/cm^2$, and still more typically between about 1 and about 10 $mW/cm^2$ (e.g., about 5 $mW/cm^2$). In addition, radiation exposure times are also varied, e.g., according to the particular monomer(s) used, the extent of double bond conversion desired, etc. To illustrate, the polymerizable compositions described herein are typically exposed to the particular radiation source from a few milliseconds to several minutes or more. Typically, the monomers of the present invention achieve substantially quantitative double bond conversion in less than 60 seconds (e.g., about 20 seconds or less) at 5 $mW/cm^2$, i.e., substantially quantitative double bond conversion is achieved at a dose typically less than 0.1 $J/cm^2$. Furthermore, polymerization temperatures are typically between 0° C. and 100° C. In preferred embodiments, polymerizations are performed at or near room temperature (e.g., 20-25° C.).

In some embodiments of the invention, a polymer produced according to the methods described herein includes compounds of formula (II):

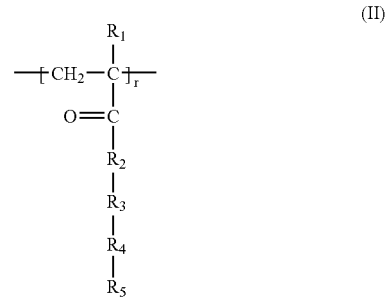

(II)

in which $R_1$-$R_5$ of each monomeric unit are independently selected as described above with respect to the monomer having the formula (I) and r is an integer greater than 1. In preferred embodiments, a polymer of the invention includes at least one monomeric unit derived from the compound of formula (I). For example, polymers can include selected combinations of mono-vinyl and multi-vinyl monomeric units. The homopolymers and copolymers of the invention can be, e.g., linear, branched, and/or cross-linked (e.g., via labile hydrogens, via non-vinyl functionalities ($R_4$), etc.). Included among the superior material properties of the polymers described herein is that they are typically substantially insoluble. Additional characteristic properties of these polymers are described throughout this disclosure.

The polymers of the invention can be included in essentially any article of manufacture, e.g., whether the polymer forms the structure of the article, a component part of the structure, a coating (e.g., a primary coating, a secondary coating, etc.) of an article or substrate, or the like. Accordingly, no attempt is made herein to describe all of the possible applications of the polymers of the present invention. However, certain exemplary embodiments are provided to further illustrate the present invention, but not to limit the invention. In particular, the polymers described herein are optionally included in articles, such as, dental restorative and other biomedical materials, fiber optic materials, lithographic materials (e.g., resists, for applications such as semiconductors, microfluidic devices, microelectronics, MEMS/NEMS, and nanolithography, etc.), membranes, adhesives, printing plates, inks, holographic materials, biomaterials, and the like. The polymers of the invention are also optionally utilized as coatings, e.g., for optical fibers, optical disks, graphic arts, paper, wood finishes, ceramics, glass, and the like. Additional aspects of the present invention are provided in, e.g., the examples below, which illustrate certain monomer synthesis and purification protocols, and provide comparisons that illustrate some of the superior properties of the monomers described herein, including high reactivities and extents of monomer conversion to polymer. Additional details relating to aspects of the present invention are also provided in, e.g., Kathryn Ann Berchtold, *Impact of Monomer Structure and Termination Kinetics on Free Radical Photopolymerizations*, Ph.D. Thesis, Department of Chemical Engineering, University of Colorado, November 2001, and Eric R. Beckel, *Novel (Meth)Acrylate Monomers for Ultrarapid Polymerization and Enhanced Polymer Properties*, Comprehensive Examination Report Submitted to the Faculty of the University of Colorado, Sep. 26, 2003, which are both incorporated by reference in their entirety for all purposes.

III. Examples

The present invention will hereinafter be described in further detail by examples. It should however be borne in mind that this invention is by no means limited to or by the examples. In particular, the synthetic and purification methods used to produce certain illustrative monomers of the present invention are provided. Monomers with identical synthetic methods are grouped under a single heading. Further, all designations of "%" mean wt. % unless otherwise specifically designated. Included in synthesis and purification sections are the 500 MHz 1H NMR frequency shifts in ppm, the boiling point (° C.), the pressure (mm Hg) at which the boiling point was determined, and the melting point, where applicable. Additionally provided are examples that illustrate the effects of secondary functionalities on monomer reactivities and extents of conversion. From the examples provided herein and the general knowledge in the art it will be apparent to one of skill how to synthesize and purify the monomers of the present invention.

A. Monomer Synthesis and Purification

1. Linear Carbonate (meth)acrylates

Example 1

Benzyl Carbonate(meth)acrylate

IUPAC name: (2-Methyl)-acrylic acid 2-benzyloxycarbonyloxy-ethyl ester
Common name: benzyl carbonate methacrylate
Abbreviation: benzyl OCO MA

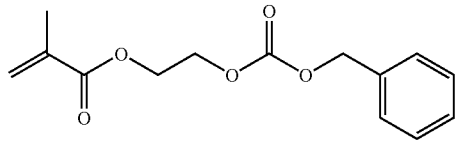

IUPAC name: Acrylic acid 2-benzyloxycarbonyloxy-ethyl ester
Common name: benzyl carbonate acrylate
Abbreviation: benzyl OCO Acr

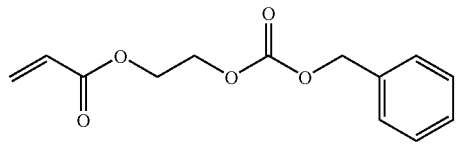

Five grams of 2-hydroxyethyl(meth)acrylate, 4 ml of triethylamine and 100 ml of methylene chloride were introduced into a three-necked flask in an ice water bath, equipped with a magnetic stirrer, reflux condenser and $N_2$ gas purge. Five grams of benzyl chloroformate were added dropwise to the solution, while maintaining the temperature below 5° C. The reaction mixture was stirred at room temperature for 6 hours and then filtered. The liquid phase was washed with 1 wt % aqueous NaOH solution, 1 wt % aqueous HCl solution, and three times with saturated NaCl solution. The product was then dried over $Na_2SO_4$ overnight. After filtering and removing the solvent, the crude product was purified by column chromatography on silica gel with a hexane/ethyl acetate eluent (3/1 by volume). The product was purified further by distillation at 0.5 mmHg and 240° C.

NMR ($CDCl_3$) (benzyl OCO MA) δ7.4(m, 5H), δ6.05(s, 1H), δ5.6(s, 1H), δ5.2(s, 2H), δ4.4(m, 4H), δ1.9(s, 3H).
NMR ($CDCl_3$) (benzyl OCO Acr) δ7.4(m, 5H), δ6.4(d, 1H), δ6.05(q, 1H), δ5.8(d, 1H), δ5.2(s, 2H), δ4.4(m, 4H).
B.P.: 140° C./0.5 mmHg 2. Aromatic Carbamates (OCN)

Example 2

Benzyl Carbamate(OCN)methacrylate

IUPAC name: 2-Methyl-acrylic acid 2-benzyloxycarbonylamino-ethyl ester
Common name: benzyl carbamate(OCN)methacrylate
Abbreviation: benzyl OCN MA

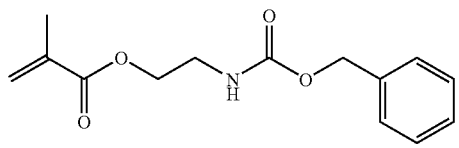

Three grams of benzyl alcohol, 50 ml of dichloromethane, and two drops of triethylamine were introduced into a three-necked flask in an ice water bath, equipped with a magnetic stirrer, reflux condenser, and $N_2$ gas purge. 2-Isocyanatoethyl methacrylate (4.5 grams) was added dropwise. The temperature of the reaction mixture was gradually raised to room temperature. The reaction was continued for three days, until the isocyanate was completely reacted, as evidenced by the disappearance of the isocyanate infrared absorption band at ca. 2270 cm$^{-1}$. After reaction completion, the organic phase was washed with 1 wt % aqueous NaOH solution, 1 wt % aqueous HCl solution, and three times with a saturated NaCl solution, followed by drying over $Na_2SO_4$ overnight. After filtering and removing the solvent under vacuum, the crude product was purified by distillation at 0.5 mmHg and 140° C. to remove the lower boiling point impurities. The temperature was then raised to 280° C. to isolate the product.

NMR (CDCl$_3$) (benzyl OCN MA) δ7.3(m, 5H), δ6.05(s, 1H), δ5.58(s, 1H), δ5.05(d, 3H), δ4.2(t, 2H), δ3.5(t, 2H), δ1.9(s, 3H).

B.P.: 170° C./0.5 mmHg

Example 3

Benzyl Carbamate(OCN)acrylate

IUPAC name: Acrylic acid 2-benzyloxycarbonylamino-ethyl ester
Common name: benzyl carbamate(OCN)acrylate
Abbreviation: benzyl OCN Acr

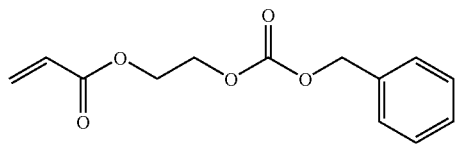

Three different methods were used to synthesize benzyl OCN acrylate. The reason for using two methods was twofold. The NMR of the pure compound revealed shoulders on two of the 1H NMR peaks at 3.4 ppm and 4.2 ppm, adjacent to the NCH$_2$ and OCH$_2$ protons. No other impurity peaks were present, but the shoulders remained unassigned. Thus, another synthetic method was designed which employed different reactants and reaction pathways. This method enabled verification of the source of the unassigned peaks. The second reason involved the availability and cost of starting materials. Method 3.1 is the least expensive in terms of raw materials, however, benzyl-N-(2-hydroxyethyl)carbamate was not readily available at the time of our initial efforts to synthesize this product. The second method (3.2) utilized also requires low cost starting materials, but produced very low yields. Method 3.3 involves the use of an expensive raw material, 1,1'-carbonyldiimidazole, but produces higher yields.

Method 3.1: Five grams of benzyl-N-(2-hydroxyethyl)carbamate, 3.6 ml of triethylamine and 80 ml of dichloromethane were introduced into a three-necked flask in an ice water bath, equipped with a magnetic stirrer, reflux condenser and $N_2$ gas purge. Acryloyl chloride (2.7 grams) was added dropwise to the solution while maintaining the temperature below 5° C. The reaction was continued at room temperature for 6 hours after the addition. The mixture was filtered, and the liquid phase was washed with 1 wt % aqueous NaOH solution, 1 wt % aqueous HCl solution, and three times with a saturated NaCl solution, followed by drying over $Na_2SO_4$ overnight. After filtering and removing the solvent under vacuum, the crude product was purified by distillation at 0.5 mmHg and 140° C. to remove the lower boiling point impurities. The temperature was then raised to 270° C. to recover the final product.

Method 3.2: Benzyl alcohol (10 ml), 8 ml of triethylamine, and 50 ml of ethyl acetate were added to a three-necked flask in an ice water bath with nitrogen purge. Under magnetic stirring, 12 ml of phenyl chloroformate were added dropwise over one hour, and the reaction mixture was stirred at room temperature for 6 hours under nitrogen purge. After the reaction was completed, 30 ml of water were added and the mixture was stirred for an additional hour to remove the unreacted chloroformate. The organic phase was then washed with 1 wt % aqueous NaOH solution, 1 wt % aqueous HCl solution, and three times with a saturated NaCl aqueous solution. After filtering, the solution was dried over $Na_2SO_4$ overnight and the solvent was evaporated under vacuum.

Ten grams of the product, 4 ml of ethanolamine, and 0.05 g of NaOH were added to a three-necked flask and heated to 100° C. for 3 hours under the nitrogen purge. Then, 50 ml of ethyl acetate was added to the reaction mixture and it was washed with 1 wt % aqueous NaOH solution, 1 wt % aqueous HCl solution, and saturated NaCl solution three times. The organic phase was dried over $Na_2SO_4$ overnight and the solvent was removed under vacuum. The crude product was purified by column chromatography on silica gel using ethyl acetate/hexane (1/3 by volume) mixture as the eluent. Five grams of the purified product, 4 ml of triethylamine, and 50 ml of ethyl acetate were introduced into a three-necked flask in an ice water bath under nitrogen purge. With magnetic stirring, 2.5 ml of acryloyl chloride were added dropwise over one hour, and the reaction mixture was stirred at room temperature for 6 hours under nitrogen purge. After the reaction was completed, 30 ml of water were added and the mixture was stirred for one hour. The organic phase was then washed with 1 wt % aqueous NaOH solution, 1 wt % aqueous HCl solution, and saturated NaCl solution three times. After the organic phase was dried over $Na_2SO_4$ overnight, the solvent was removed under vacuum. This crude product was purified by distillation as described in Method 5.1.

Method 3.3: 3 grams of 1,1'-carbonyldiimidazole and 50 ml of dichloromethane were introduced into a three-necked flask in an ice water bath under nitrogen purge. With magnetic stirring, two ml of benzyl alcohol were added dropwise over one hour and the reaction mixture was stirred at room temperature for 12 hours under nitrogen purge. After the reaction was completed, 1.2 ml of ethanolamine was added and the mixture was stirred for 48 hours. Then, the organic phase was washed with 1 wt % aqueous NaOH solution, 1 wt % aqueous HCl solution, and saturated NaCl solution three times. The product was dried over $Na_2SO_4$ overnight and the solvent was evaporated under vacuum. The crude product was recrystallized from chloroform/hexane (1/4 by volume) solution. Five grams of the recrystallized product, 3.6 ml of triethylamine and 80 ml of dichloromethane were introduced into a three-necked flask in an ice water bath, equipped with a magnetic stirrer, reflux condenser and $N_2$ gas purge. 2.7 grams of acryloyl chloride were added dropwise to the solution while maintaining the temperature below 5° C. The reaction mixture was stirred at room temperature for 6 hours. The mixture was filtered, and the liquid phase was washed with 1 wt % aqueous NaOH solution, 1 wt % aqueous HCl solution, and three times with saturated NaCl solution followed by drying over $Na_2SO_4$ overnight. After filtering and removing the solvent, the product was distilled at 0.5 mmHg and 140° C. to remove lower boiling point impurities. The temperature was then raised to 270° C. to recover the product.

NMR (CDCl₃) (Benzyl OCN Acr) δ7.3(m, 5H), δ6.4(d, 1H), δ6.05(q, 1H), δ5.8(d, 1H), δ5.05(d, 3H), δ4.2(t, 2H), δ3.5(m, 2H).

B.P.: 160° C./0.5 mmHg.

Example 4

Diphenyl Carbamate(OCN)methacrylate

IUPAC name: 2-Methyl-acrylic acid 2-benzhydryloxycarbonylamino-ethyl ester
Common name: diphenyl carbamate(OCN)methacrylate
Abbreviation: diphenyl OCN MA

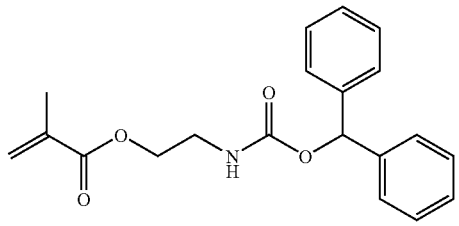

Seven grams of benzhydrol, 50 ml of dichloromethane and two drops of triethylamine were introduced into a three-necked flask in an ice-water bath, equipped with a magnetic stirrer, reflux condenser and N2 gas purge. 2-Isocyanatoethyl methacrylate (5 ml) was added dropwise and the temperature of the reaction mixture was gradually raised to room temperature. The reaction was followed for three days until the isocyanate IR peak at 2270 cm⁻¹ completely disappears. The mixture was then washed with 1 wt % aqueous NaOH, 1 wt % aqueous HCl and with saturated NaCl solution three times. The organic phase was dried over Na₂SO₄ overnight. After removing the solvent, lower boiling point impurities were distilled off at 0.5 mmHg and 140° C. The product was obtained at a bath temperature of 300° C. and 0.5 mm Hg pressure.

NMR (CDCl₃) (diphenyl OCN MA) δ7.3(m, 10H), δ6.77 (s, 1H), δ6.05(s, 1H), δ5.52(s, 1H), δ5.05(s, 1H), δ4.21(t, 2H), δ3.42(m, 2H), δ1.9(s, 3H).

B.P.: 183° C./0.5 mmHg
M.P.: 48° C.

Example 5

Diphenyl Carbamate(OCN)acrylate

IUPAC name: Acrylic acid 2-benzhydryloxycarbonylamino-ethyl ester
Common name: diphenyl carbamate(OCN)acrylate
Abbreviation: diphenyl OCN Acr

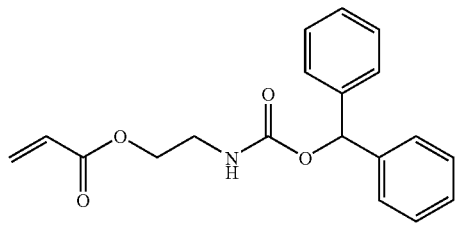

Two methods were also used to synthesize diphenyl OCN acrylate. Method 5.1 is the least expensive, but also resulted in the lowest yield. Method 5.2 uses an expensive raw material 1,1'-carbonyldiimidazole but has the advantage of producing higher yields.

Method 5.1: Benzhydrol (10 ml), 7 ml of triethylamine, and 50 ml of ethyl acetate were introduced into a three-necked flask in an ice water bath with nitrogen purge. Under magnetic stirring, 7 ml of phenyl chloroformate were added dropwise over one hour, and the reaction mixture was stirred at room temperature for 6 hours under nitrogen purge. After the reaction was completed, 30 ml of water were added and the mixture was stirred for one hour. Then, the organic phase was washed with 1 wt % aqueous NaOH solution, 1 wt % aqueous HCl solution, and saturated NaCl solution three times. The organic phase was dried with Na₂SO₄ overnight and the solvent was evaporated under vacuum. Ten grams of the product, 5 ml of ethanolamine and 0.05 g of NaOH were added to a three-necked flask and heated to 100° C. for 6 hours under nitrogen purge. Then, 50 ml of ethyl acetate was added to the reaction mixture and the resultant solution was washed with 1 wt % aqueous NaOH solution, 1 wt % aqueous HCl solution, and saturated NaCl solution three times. The organic phase was dried with Na₂SO₄ overnight and the solvent was removed under vacuum. The crude product was purified using column chromatography on silica gel using ethyl acetate/hexane (1/3 by volume) as the eluent. The product was further purified by recrystallization from chlorform/hexane (1/4 by volume) solution. Five grams of the purified product, 3 ml of triethylamine, and 50 ml of ethyl acetate were added to a three-necked flask in an ice water bath under nitrogen purge. With magnetic stirring, 2 ml of acryloyl chloride were added dropwise over one hour, and the reaction mixture was stirred at room temperature for 6 hours under nitrogen purge. After the reaction was completed, 30 ml of water were added and the mixture was stirred for one hour. Then, the organic phase was washed with 1 wt % aqueous NaOH solution, 1 wt % aqueous HCl solution, and saturated NaCl solution three times. The organic phase was dried over Na₂SO₄ overnight and the solvent was removed under vacuum. The lower boiling point impurities were distilled off at 0.5 mmHg and 140° C. Then, the temperature was raised to 290° C. to get the product.

Method 5.2: 1,1'-Carbonyldiimidazole (4.4 g) and 50 ml of dichloromethane were introduced into a three-necked flask in an ice water bath under nitrogen purge. With magnetic stirring, 5 grams of benzhydrol dissolved in 50 ml of dichloromethane were added dropwise over one hour, and the reaction mixture was stirred at room temperature for 12 hours under nitrogen purge. After the reaction was completed, 1.7 ml of ethanolamine was added to the flask and the reaction mixture was stirred for 48 hours. The organic phase was subsequently washed with 1 wt % aqueous NaOH solution, 1 wt % aqueous HCl solution, and saturated NaCl solution three times. The product was dried over Na₂SO₄ overnight and the solvent was removed under vacuum. The crude product was recrystallized from chloroform/hexane (1/4 by volume) solution. Seven grams of the above product, 3.6 ml of triethylamine and 80 ml of dichloromethane were introduced into a three-necked flask in ice water bath equipped with a magnetic stirrer, reflux condenser and N₂ gas purge. 2.7 grams of acryloyl chloride were added dropwise to the solution maintaining the temperature below 5° C. over two hours. The solution was stirred at room temperature for 6 hours. The mixture was filtered and the liquid was washed with 1 wt % aqueous NaOH solution, 1 wt % aqueous HCl solution, and saturated NaCl solution three times. The organic phase was dried over Na₂SO₄ overnight and the solvent was removed under vacuum. The lower boiling point impurities were distilled off at 0.5 mmHg and 140° C. and the temperature raised to 290° C. to get the product.

NMR (CDCl$_3$) (diphenyl OCN Acr) δ7.3(m, 10H), δ6.8(s, 1H), δ6.4(d, 1H), δ6.05(q,1H), δ5.8(d, 1H), δ5.05(s, 1H), δ4.2(t, 2H), δ3.5(m, 2H).

B.P.: 178° C./0.5 mmHg
M.P.: 58-59° C.

3. N-Substituted Carbamate Acrylates

Example 6

N-Methylbenzyl Carbamate(NCO)Acrylate

IUPAC name: Acrylic acid 2-(benzyl-methyl-carbamoyloxy)-ethyl ester
Common name: N-methyl benzyl carbamate acrylate
Abbreviation: benzyl N(CH$_3$)CO Acr

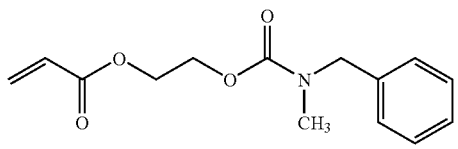

Ethylene glycol (2 g) and 100 ml of methylene chloride were added to a three-necked flask in an ice-water bath under nitrogen purge. Five grams of 1',1'-carbonydiimidazol were added over two hours and the reaction mixture was stirred at room temperature for 48 hours under nitrogen purge. After the reaction was completed, 4 g of N-benzylmethylamine was added and the mixture was stirred for 48 hours. The organic phase was washed with 1 wt % aqueous NaOH solution, 1 wt % aqueous HCl solution, and three times with saturated NaCl aqueous solution. The organic phase was dried over Na$_2$SO$_4$ overnight and evaporated under vacuum to remove the solvent. The crude product was purified by chromatography on silica gel with hexane/ethyl acetate (3/1 by volume) elution. Six grams of the product, 5 ml of triethylamine, and 80 ml of dichloromethane were added to a three-necked flask, equipped with a magnetic stirrer and N$_2$ gas purge in an ice-water bath. Acryloyl chloride (3.5 grams) was added dropwise to the solution carefully over two hours to maintain the temperature below 5° C., and it was reacted at room temperature for 6 hours. The mixture was filtered and the filtrate was washed with 1 wt % of aqueous NaOH and 1 wt % of aqueous HCl solutions. After washing three times with saturated NaCl solution, it was dried over Na$_2$SO$_4$ overnight. The solvent was removed and the crude product was purified by chromatography on silica gel with hexane/ethyl acetate (3/1 by volume) elution.

NMR (CDCl$_3$) (benzyl N(CH$_3$)CO Acr) δ7.3(m, 5H), δ6.4 (q, 1H), δ6.05(m, 1H), δ5.8(t, 1H), δ4.4(m, 6H), δ2.9(d, 3H).

Example 7

N-Ethylphenyl Carbamate(OCN)Acrylate

IUPAC name: 2-(N-ethylphenoxycarbonylamino)ethyl prop-2-enoate
Common name: N-ethylphenyl carbamate acrylate
Abbreviation: phenyl OCN(C$_2$H$_5$)Acr

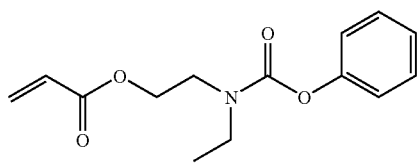

Ten grams of 2-(ethylamino)ethanol (98%), 18 ml of triethylamine and 150 ml of chloroform were added to a round-bottom flask with magnetic stirring in an ice bath. Chlorotrimethylsilane (14 ml, 99+%) was introduced to the flask slowly. The reaction was continued for 10 minutes after the addition of all chlorotrimethylsilane. The triethylamine salt was removed by filtration and the trimethylsilyl ethylamine was obtained. The product, 18 ml of triethylamine and 200 ml of methylene chloride were mixed in a round-bottom flask under nitrogen purge with magnetic stirring in an ice-water bath. 20 ml of phenyl chloroformate (99%) was introduced into the flask dropwise over one hour and the reaction was performed at room temperature overnight. After filtering the triethylamine salt, the filtrate was mixed with 10 ml of methanol, 10 ml of deionized water and a small amount of triethylamine to adjust the pH to above 8. At room temperature, the resultant Nethylphenyl carbamate trimethylsilane was hydrolyzed in two days. After removal of solvent, the hydroxyethyl N-ethylcarbamate benzene was extracted with ethyl acetate. This solution was mixed with 30 ml of triethylamine and 50 ml of methylene chloride in a round-bottom flask under nitrogen purge with magnetic stirring in an ice water bath. Acryloyl chloride 15 ml was added into the flask over one hour and then reacted at room temperature overnight. After the reaction mixture was filtered, the solution was washed with 1 wt % NaOH solution, 1 wt % HCl solution, and saturated NaCl solution. The organic phase was dried with Na$_2$SO$_4$ overnight and the crude product was purified by chromatography on silica gel with the elution of hexane/ethyl acetate solution (4/1 by volume). The pure product is a colorless liquid.

NMR (CDCl$_3$) (phenyl OCN(C2H5)Acr) δ7.3(m, 5H), δ6.4(d, 1H), δ6.05(q, 1H), δ5.8(d, 1H), δ4.2(t, 2H), δ3.5-3.7 (m, 4H), δ1.1(m, 3H).

4. Benzyl Ureas

Example 8

Benzyl Urea Methacrylate

IUPAC name: 2-Methyl-acrylic acid 2-(3-benzyl-ureido)-ethyl ester
Common name: benzyl urea methacrylate
Abbreviation: benzyl NCN MA

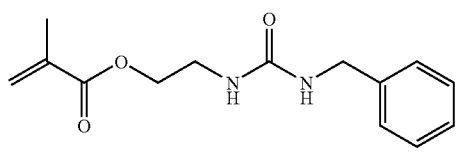

Three grams of benzylamine and 100 ml of chloroform were added to a three-necked flask, equipped with a magnetic stirrer, reflux condenser and N$_2$ gas purge at 0° C. 2-Isocyanatoethyl methacrylate (4.5 g) was added dropwise to the solution while carefully maintaining the temperature below 5° C. The reaction was continued at room temperature for 12 hours. The product was then washed with 1 wt % aqueous NaOH and HCl solutions sequentially and three times with a saturated NaCl solution. The organic phase was then dried over Na$_2$SO$_4$ overnight. After removing the solvent under vacuum, the crude product was purified by recrystallization from hexane/chloroform solution (2/1 by volume).

NMR(CDCl$_3$) (benzyl NCN MA) δ7.3(m, 5H), δ6.05(s, 1H), δ5.55(s, 1H), δ4.3(s, 2H), δ4.2(t, 2H), δ3.5(t, 2H), δ1.9 (s, 3H).

M.P: 70° C.

Example 9

Benzyl Urea Acrylate

IUPAC name: Acrylic acid 2-(3-benzyl-ureido)-ethyl ester
Common name: benzyl urea acrylate
Abbreviation: benzyl NCN Acr

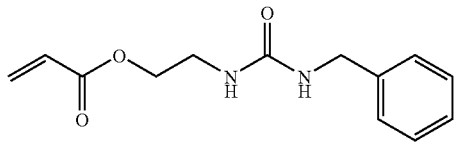

Ethanolamine and 100 ml of methylene chloride were added to a three necked flask, equipped with a magnetic stirrer, reflux condenser and N$_2$ gas purge, and placed in an ice-water bath. Five grams of benzyl isocyanate were introduced dropwise into the flask while maintaining the temperature of the solution below 5° C. The reaction mixture was stirred at room temperature for 12 hours. Triethylamine (5.4 ml) was added to the reaction mixture under nitrogen purge and the flask was again placed in an ice-water bath. Acryloyl chloride (3.5 g) was added and the reaction continued at room temperature for 6 hours. The mixture was washed with 1 wt % aqueous NaOH and HCl solutions, sequentially, followed by saturated NaCl solution three times. Then, the mixture was dried over Na$_2$SO$_4$ overnight, and after removing the solvent under vacuum, the crude product was recrystallized from hexane/chloroform solution (2/1 by volume).

NMR (CDCl$_3$) (benzyl NCN Acr) δ7.3(m, 5H), δ6.4(d, 1H), δ6.05(q, 1H), δ5.8(d, 1H), δ4.3(s, 2H), δ4.2(t, 2H), δ3.5(t, 2H).

M.P: 74-76° C.

B. Effect of Non-Vinyl Functionalites

Example 10

Addition of a Benzyl Carbonate or Carbamate Moiety to an Ethyl Acrylate Core

Figure 1:
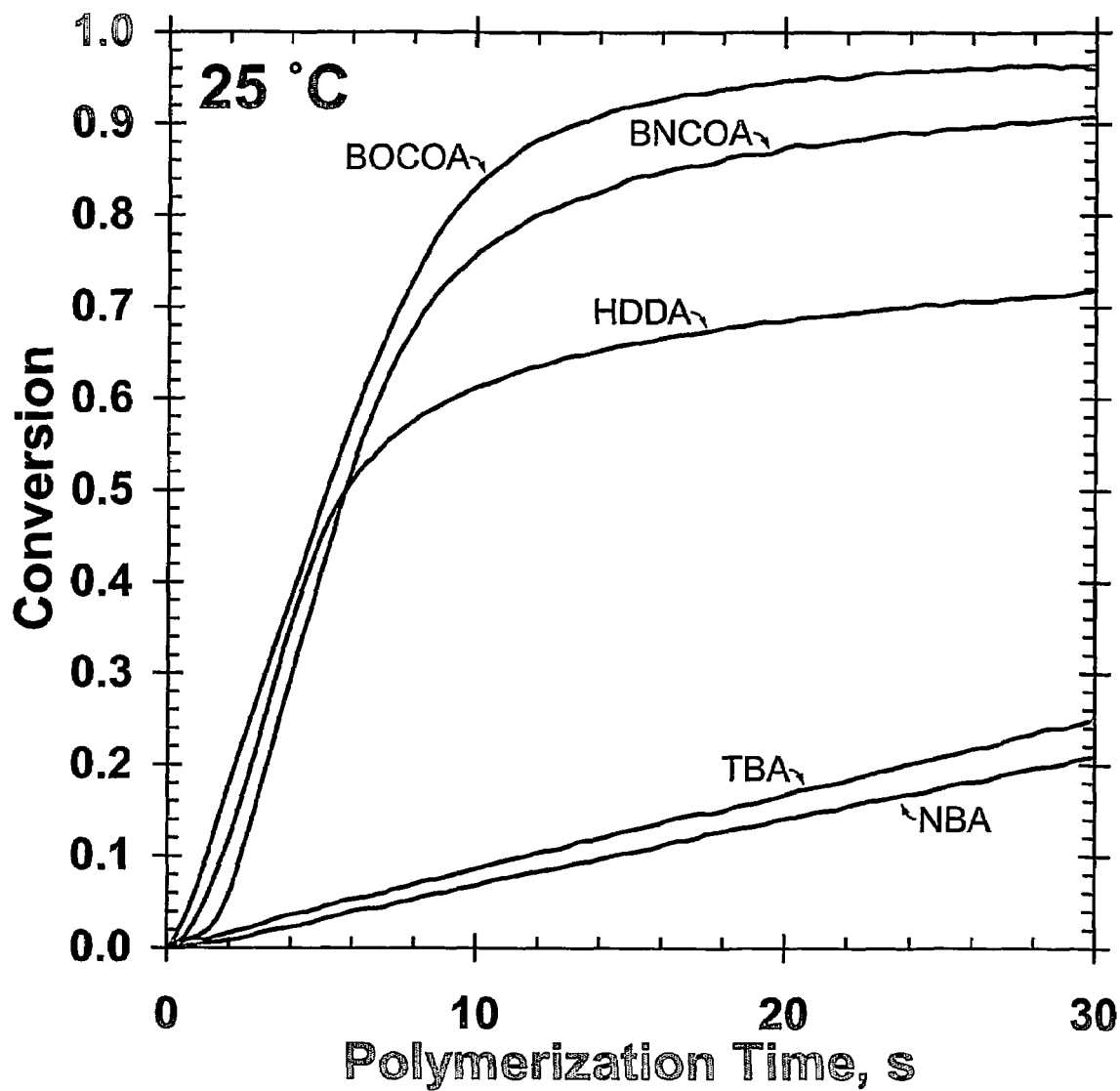
FIG. 1 is a data graph (abscissa—polymerization time (seconds); ordinate—extent of conversion) that illustrates the effect of secondary functionality ($R_4$) addition and benzyl end group ($R_5$) substitution onto an ethyl ($R_3$) acrylate core. The polymerizations were performed at 25° C. with an initiator concentration of 0.1 wt % and a light intensity of 5 mW/cm².

Although the monomers of the present invention include only a single vinyl polymerizable moiety, they form complex, 3-D, insoluble, polymer networks on time scales that rival those of the industry standard, multi-vinyl containing monomers. For example, the addition of a benzyl carbonate or carbamate moiety to an ethyl acrylate core enhances the polymerization rate by an order of magnitude over that of typical aliphatic and aromatic mono-vinyl acrylates (FIG. 1). In fact, the polymerization rate is increased to the point that these mono-vinyl monomers polymerize as fast, and faster than conventional multi-vinyl monomers that are prevalent in commercial applications. This feature is illustrated in a comparison of polymerizations of 1,6 hexanediol diacrylate (HDDA) with benzyl carbonate and carbamate substituted monoacrylates in FIG. 1. As shown, benzyl NCO acrylate (BNCOA) and benzyl OCO acrylate (BOCOA) are presented. The divinyl polymerization of HDDA, mono-vinyl n-butyl acrylate (NBA), and t-butyl acrylate (TBA) polymerizations are also shown for comparison. The polymerizations were conducted at 25° C. with an initiator concentration of 0.1 wt % and a light intensity of 5 mW/cm$^2$.

Additionally, increased polymerization rates, as typically attained via an increase in the number of vinyl functionalities in a given monomer, are commonly also accompanied by a decrease in the maximum attainable double bond conversion. Another advantage of the monomers of the invention is the combination of their high reactivity with their ability to reach nearly quantitative double bond conversion. This feature translates into materials with low residual/leachable monomer content, and thus, lower toxicity and a higher resistance to material property changes over time, i.e., an increase in the lifetime or durability of the material. The rapid and complete polymerization of these novel materials also translates into minimal reaction exposure times and intensities, traits that have significance for a wide range of curing applications, e.g., filled and multilayer polymerizations, in addition to economic and environmental implications.

Example 11

Figure 2:
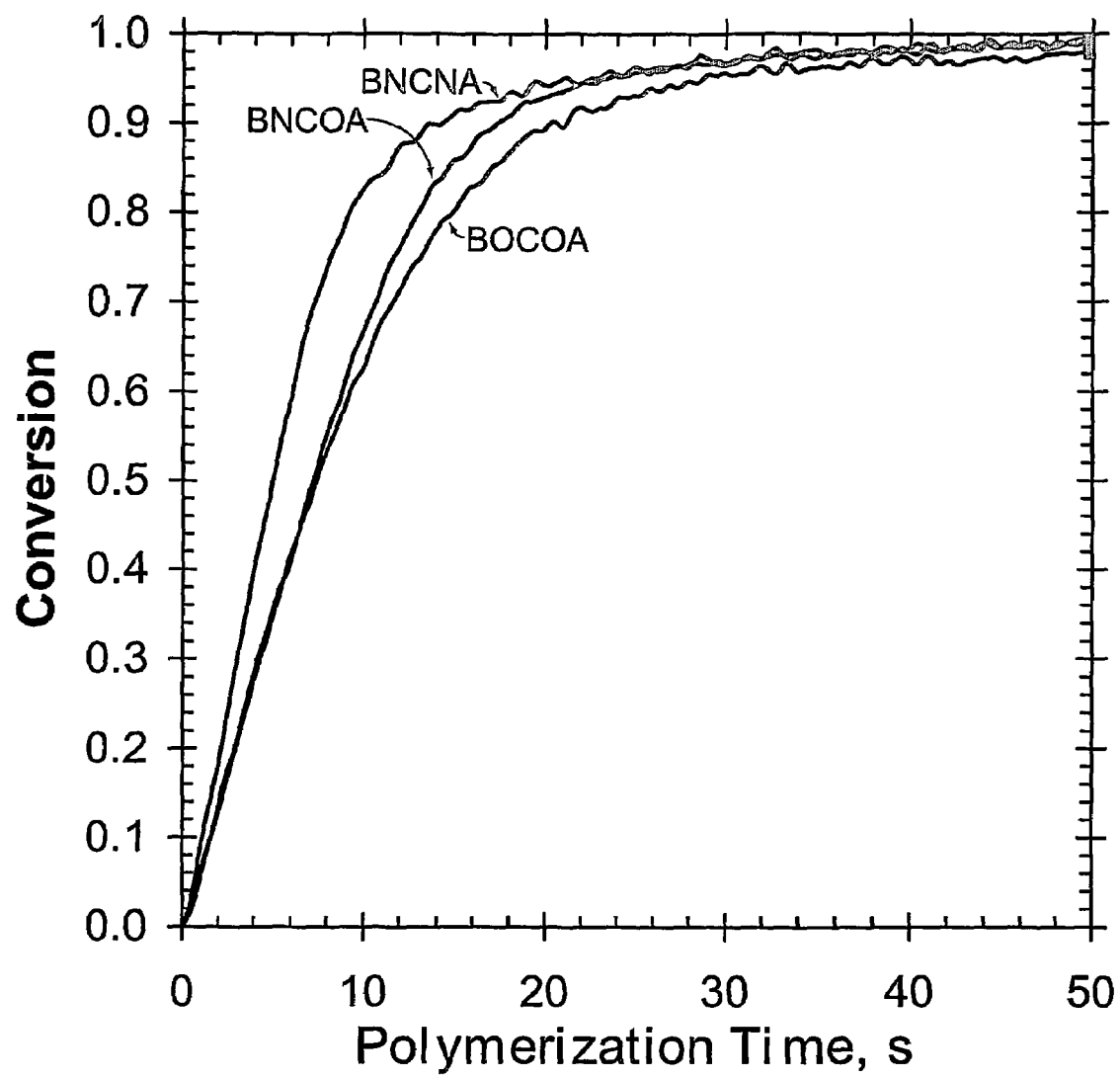
FIG. 2 is a data graph (abscissa—polymerization time (seconds); ordinate—extent of conversion) that shows the effect of the secondary functionality ($R_4$) in a series of benzyl ($R_5$) ethyl ($R_3$) acrylates. The polymerizations were performed at 67° C. with an initiator concentration of 0.1 wt % and a light intensity of 5 mW/cm². BNCNA was polymerized at 75° C.

Effect of Secondary Functionality (R$_4$) in a Series of Benzyl (R$_5$) Ethyl (R$_3$) Acrylates Monomer reactivity and polymerization characteristics are manipulated over a wide range by variations in the character of the R$_4$ and R$_5$ moieties. For example, substitution of a urea for the carbamate and carbonate secondary functionalities (R$_4$) presented in FIG. 1, i.e., benzyl NCN acrylate, leads to an increase in the polymerization rate of nearly 1.5 times over the carbamate and carbonate benzyl acrylate polymerizations (FIG. 2). As shown in FIG. 2, benzyl OCO acrylate (BOCOA), benzyl NCO acrylate (BNCOA), and benzyl NCN acrylate (BNCNA) are presented. The polymerization conditions included an initiator concentration of 0.1 wt % and a light intensity of 5 mW/cm$^2$. The polymerization of benzyl OCO acrylate and benzyl NCO acrylate were performed at 67° C., but due to the high melting point of the urea monomer (i.e., ~75° C.), the polymerization of benzyl NCN acrylate was conducted at 75° C.

Example 12

Figure 3:
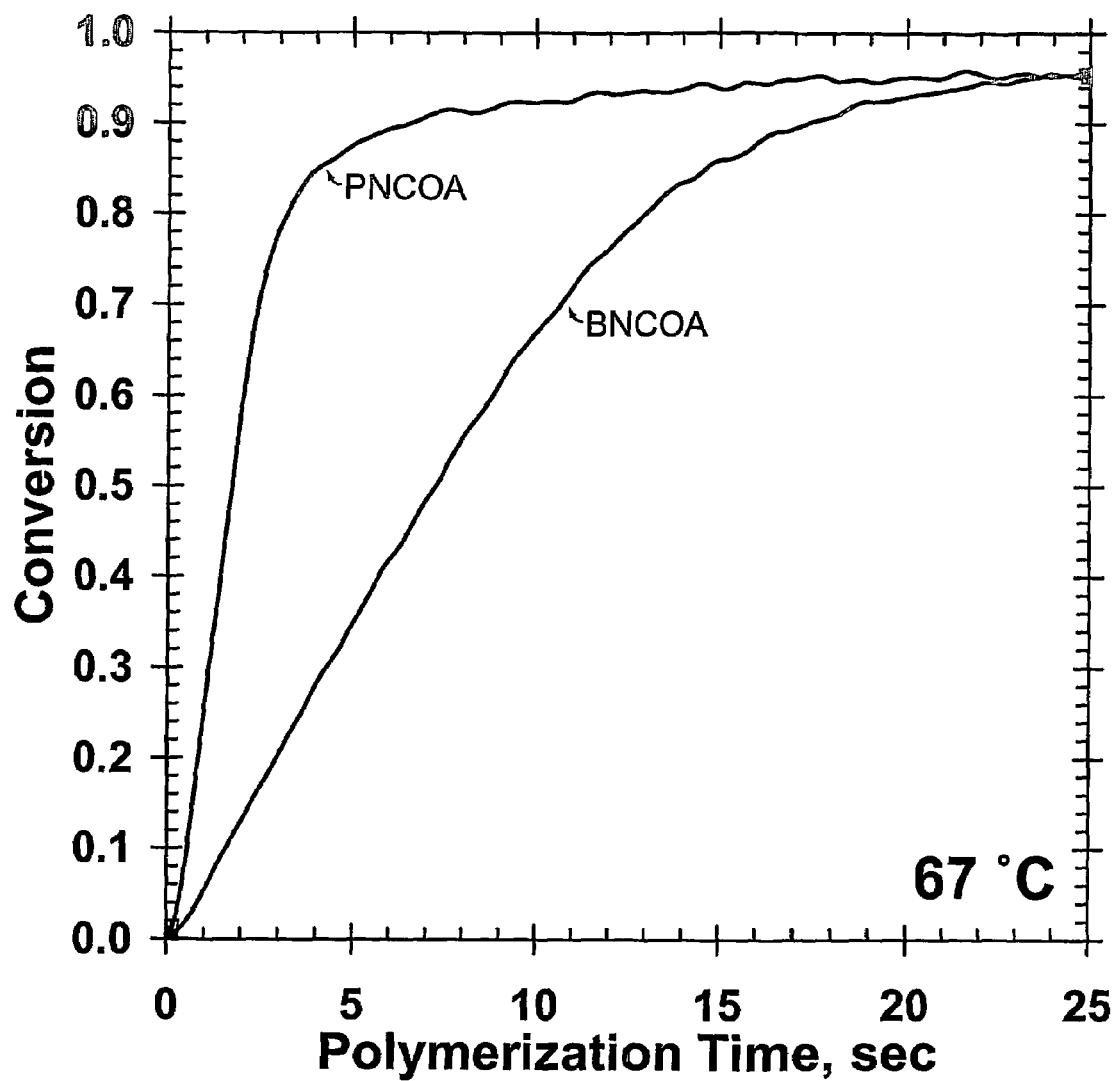
FIG. 3 is a data graph (abscissa—polymerization time (seconds); ordinate—extent of conversion) that illustrates the effect of varying the aromatic end group ($R_5$) on the polymerization kinetics of carbamate acrylate polymerization. The polymerizations were performed at 67° C. with an initiator concentration of 0.1 wt % and a light intensity of 5 mW/cm².

Effect of Varying the Aromatic End Group (R$_5$) on the Polymerization Kinetics of Carbamate Acrylate Polymerization Dramatic rate increases are also realized with variations in the chemistry and electronic structure of the end group substituent. A factor of four increase in the maximum polymerization rate is obtained by the simple substitution of a phenyl for a benzyl end group in the carbamate ethyl acrylate materials (FIG. 3). In particular, a comparison of benzyl NCO acrylate (BNCOA) and phenyl NCO acrylate (PNCOA) is presented. The polymerization conditions included an initiator concentration of 0.1 wt %, a light intensity of 5 mW/cm$^2$, and a temperature of 67° C.

Example 13

Effects of Methacrylate Vinyl Functionalities

Figure 4A:
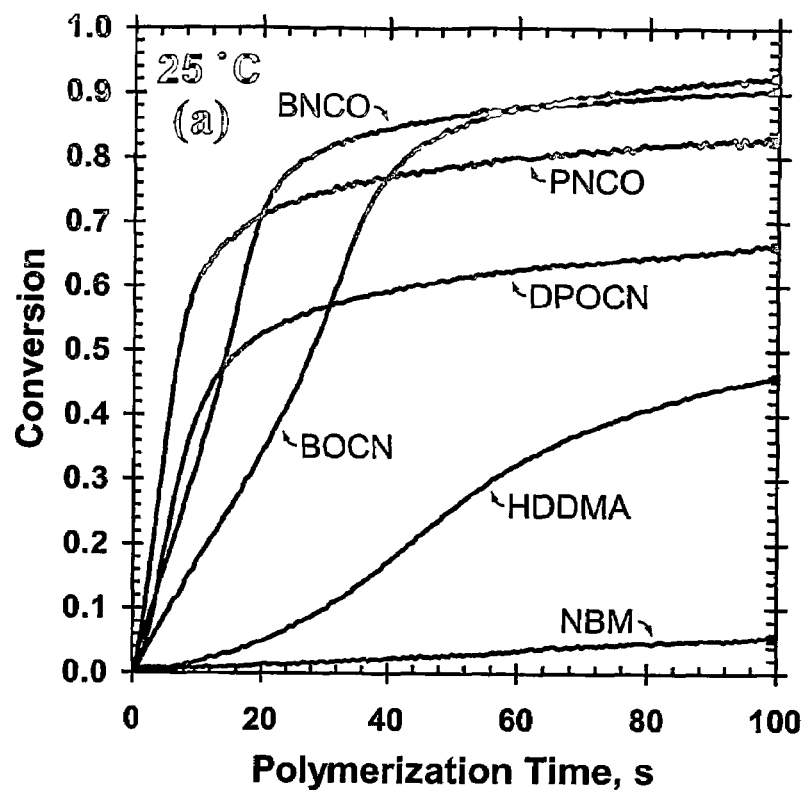
FIGS. 4A and B are data graphs (abscissa—polymerization time (seconds); ordinate—extent of conversion) that show the effects of methacrylate vinyl functionalities. The polymerizations were performed at (A) 25° C. and (B) 67° C. with an initiator concentration of 0.1 wt % and a light intensity of 5 mW/cm².
Figure 4B:
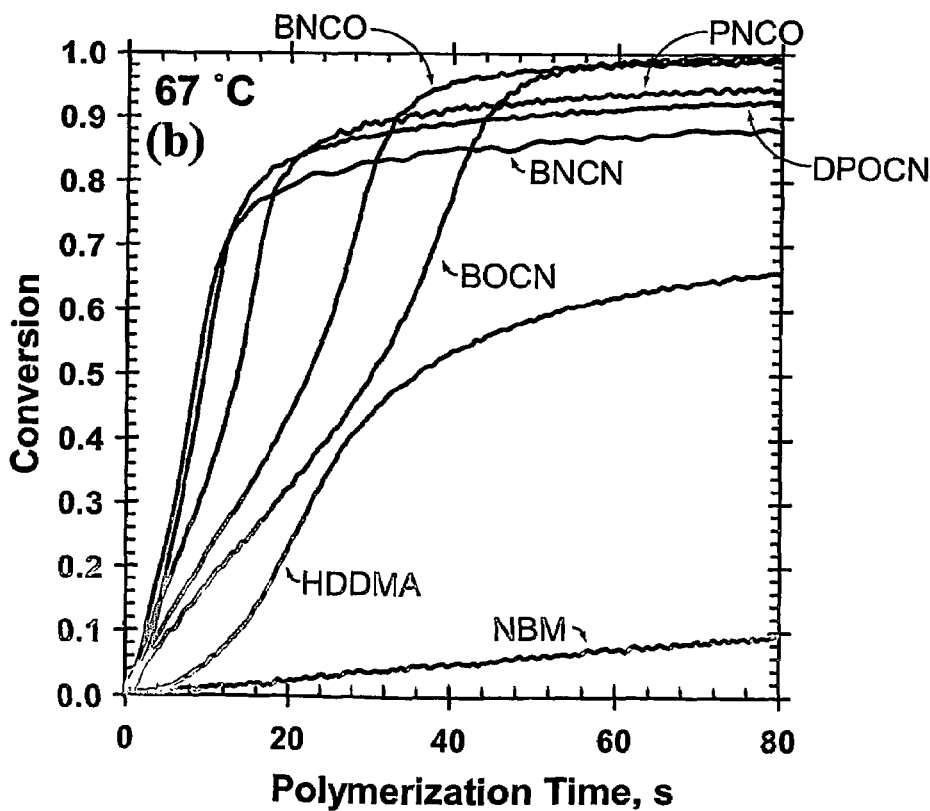

The rate enhancements of the present invention are not limited to acrylate vinyl chemistries, they are also realized in materials with methacrylate, acrylamide and methacrylamide vinyl functionalities. As an illustration, this example shows rate enhancements achieved with methacrylate vinyl functionalities. As for the acrylate materials (described above), carbamate monomers such as diphenyl, phenyl, and benzyl carbamate methacrylates increase maximum polymerization rates by an order of magnitude over HDDMA, while simultaneously increasing the maximum attainable conversion by 20-42% (FIG. 4). In particular, FIG. 4 shows comparisons of diphenyl OCN (DPOCN), phenyl NCO (PNCO), benzyl NCN (BNCN, FIG. 4B only), benzyl NCO (BNCO), and benzyl OCN (BOCN) ethyl methacrylate monomers with the mono-vinyl n-butyl methacrylate (NBM) and divinyl HDDMA polymerizations. Variations in secondary functionality also contribute to monomer reactivity in the methacrylates, as evidenced by, e.g., the benzyl urea (NCN) polymerization (FIG. 4B). The polymerization conditions included a light intensities of 5 mW/cm$^2$ and initiator concentrations of 0.1 wt %. The polymerization temperatures were 25° C. (FIG. 4A) and 67° C. (FIG. 4B), with the exception of benzyl NCN MA in FIG. 4B which was polymerized at 75° C.

Example 14

Figure 5:
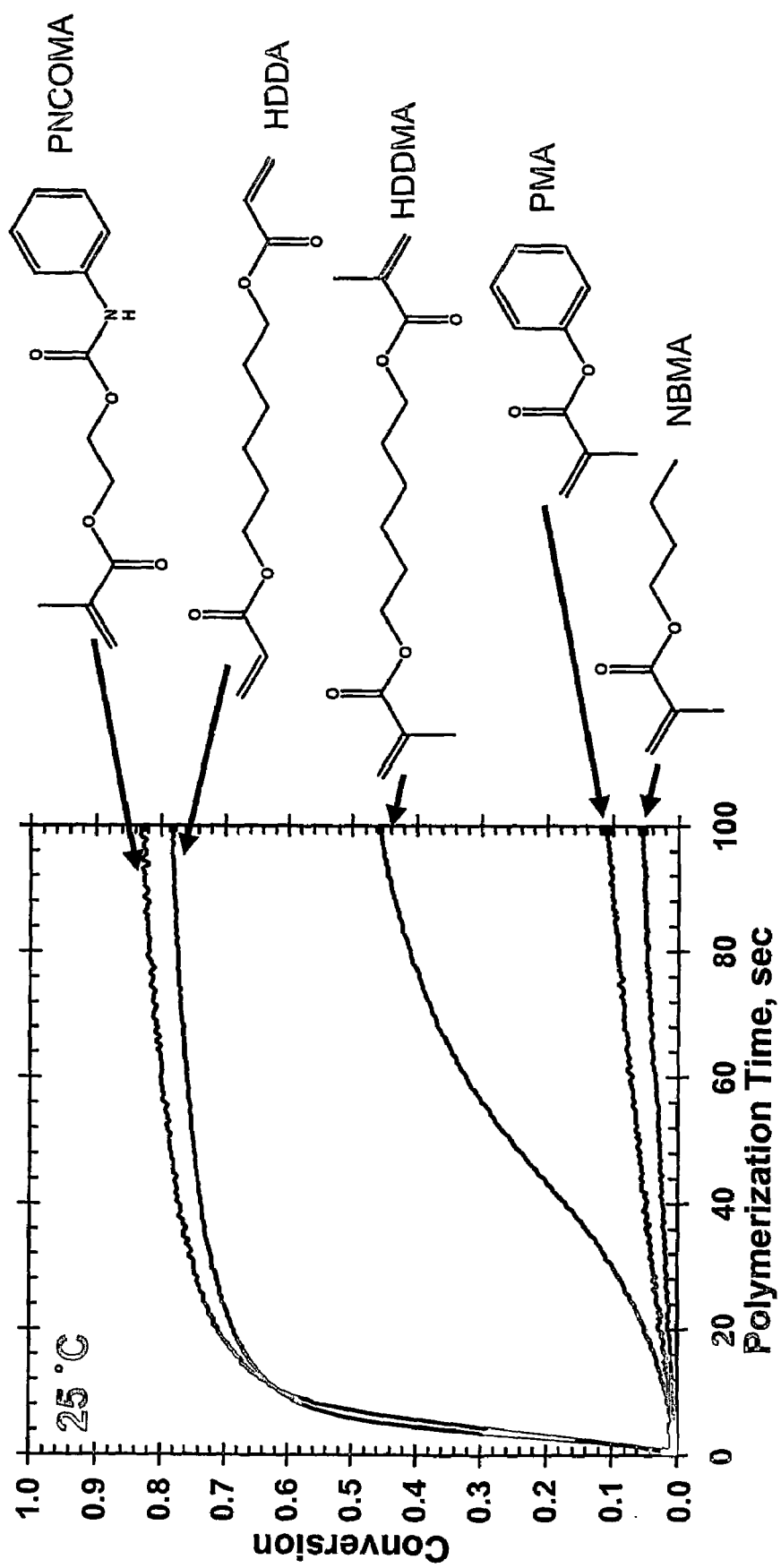
FIG. 5 is a data graph (abscissa—polymerization time (seconds); ordinate—extent of conversion) that illustrates a comparison of phenyl carbamate ethyl methacrylate with other mono and divinyl (meth)acrylates. The polymerizations were performed at 25° C. with an initiator concentration of 0.1 wt % and a light intensity of 5 mW/cm².

Comparison of Phenyl Carbamate Ethyl Methacrylate with Other Mono and Divinyl(meth)acrylates Even though methacrylates are typically less reactive in free radical polymerizations than their acrylate counterparts, the monomethacrylate monomers of the present not only outperform industry standard multimethacrylate polymerizations, but also rival diacrylate polymerizations. One such example is presented in FIG. 5. As shown, a comparison of phenyl carbamate ethyl methacrylate (PNCOMA) with other mono and divinyl (meth)acrylates is presented. The other mono-vinyl polymerizations presented are n-butyl methacrylate (NBMA) and phenyl methacrylate (PMA). The divinyl HDDA and HDDMA polymerizations are also presented. The polymerization conditions includes temperatures of 25° C., light intensities of 5 mW/cm$^2$, and initiator concentrations of 0.1 wt %.

Example 15

(meth)acrylate Monomers for Ultrarapid Polymerization and Enhanced Polymer Properties Introduction Ultraviolet light is known to be one of the most efficient methods to initiate polymeric reactions in the presence of a photoinitiator. Photopolymerizations are advantageous because the chemistry of the materials can be tailored to design liquid monomers for ultrarapid polymerization into a solid polymer material. One way to achieve rapid photopolymerizations is to utilize multifunctional (meth)acrylate monomers, which form highly crosslinked polymers; however, these monomers typically do not achieve complete functional group conversion (Decker, C.; Moussa, K. Macromolecules 1989, 22, 4455, Tryson, G. R.; Shultz, A. R. J. Poly. Sci: Poly. Phys. 1979, 17, 1043, and Young, J. S.; Kannurpatti, A. R.; Bowman, C. N. Macromol. Chem. Phys. 1998, 199, 1043). Decker et al. developed monovinyl acrylate monomers that display polymerization kinetics that rival those of multifunctional acrylate monomers. These acrylate monomers incorporate secondary functionalities and end groups such as carbonates (Decker, C.; Moussa, K. Makromol. Chem. 1991, 192, 507, Decker, C.; Moussa, K. Eur. Poly. J. 1991, 27, 403, Decker, C.; Moussa, K. Eur. Poly. J. 1991, 27, 881, and Moussa, K.; Decker, C. J. Poly. Sci.: Poly. Chem. 1993, 31, 2197), carbamates (Decker, C.; Moussa, K. Macromolecules 1989, 22, 4455, Decker, C.; Moussa, K. Eur. Poly. J. 1991, 27,403, and Decker, C.; Moussa, K. Eur. Poly. J. 1991, 27, 881), cyclic carbonates (Decker, C.; Moussa, K. Makromol. Chem. 1991, 192, 507, Brosse, J. C.; Chevalier, S.; Couvert, D.; Decker, C.; Moussa, K.; Societe Nationale des Poudres et Explosifs, 1989, Decker, C.; Moussa, K. Makromol. Chem. Rapid Comm. 1990, 11, 159, and Moussa, K.; Decker, C.; Brosse, J.; Chevalier, S.; Couvert, D. Societe Nationale des Pourdres et Explosifs, 1991), and oxazolidones (Decker, C.; Moussa, K. Eur. Poly. J. 1991, 27, 403, Decker, C.; Moussa, K. Eur. Poly. J. 1991, 27, 881, and Moussa, K.; Decker, C. J. Poly. Sci.: Poly. Chem. 1993, 31, 2197), which promote the increased polymerization kinetics of these monomers. In addition to the polymerization kinetics, these monovinyl monomers form crosslinked polymers, which are characterized by having high strength and high flexibility. Unfortunately, the exact mechanism or mechanisms responsible for the polymerization kinetics and crosslinking are not well understood.

Figure 6:
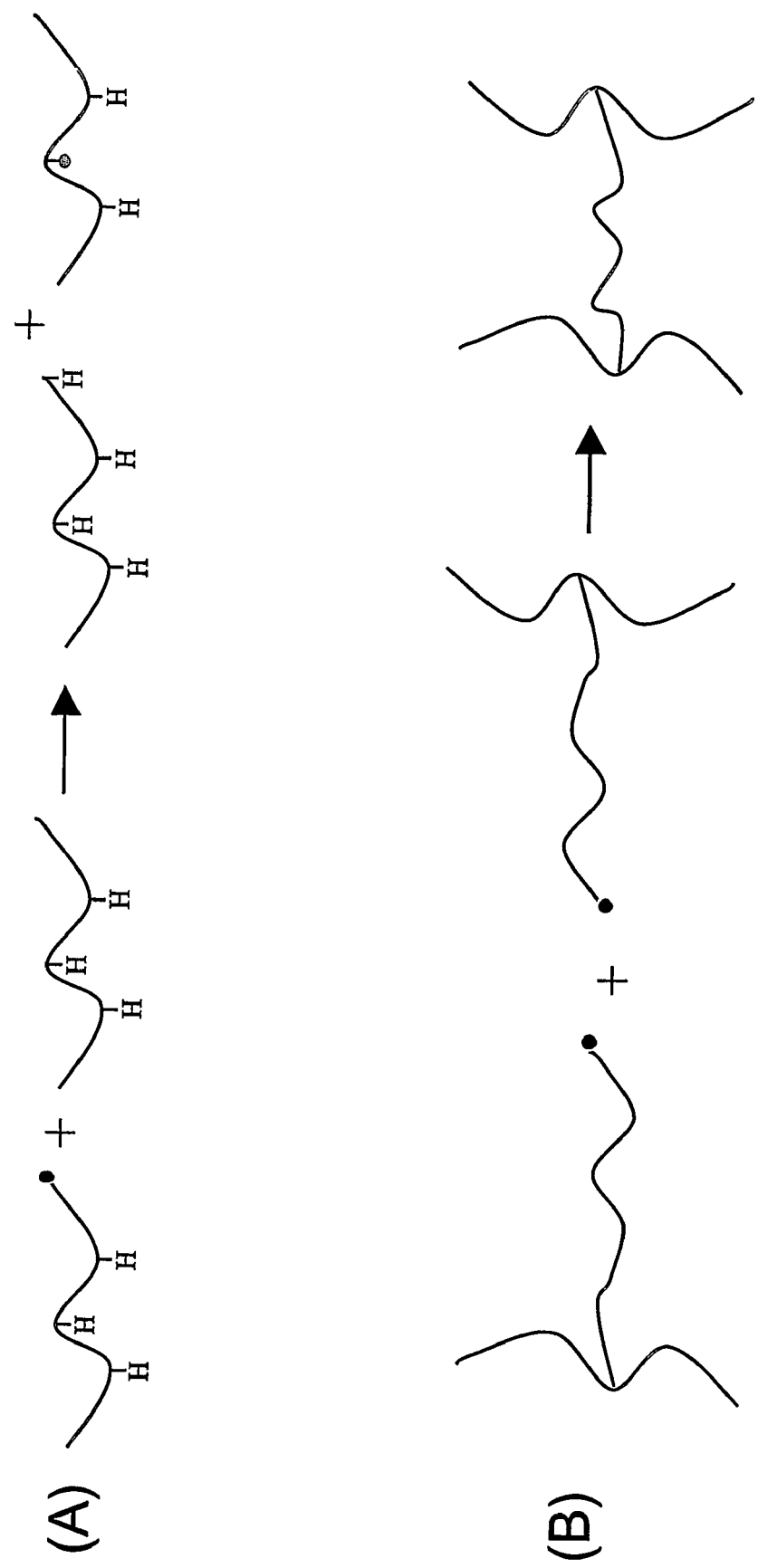
FIG. 6 schematically depicts a chain transfer reaction.

Several mechanistic theories have been proposed in an attempt to explain the enhanced reactivities of these monomers. Decker et al. proposed a possible hydrogen abstraction reaction due to labile hydrogens associated with the secondary functionalities and end groups (Moussa, K.; Decker, C. J. Poly. Sci.: Poly. Chem. 1993, 31, 2197 and Decker, C. Nucl. Inst. Methods Phys. Res. B 1999, 151, 22). These labile hydrogens undergo a chain transfer reaction, creating branches and thus, radical sites for crosslinking. Crosslinking by chain transfer is schematically depicted in FIG. 6, which shows hydrogen abstraction/chain transfer in (A) and crosslink formation in (B). The maximum theoretical crosslink concentration from this H-abstraction/chain transfer with subsequent termination reaction is on the order of the initiator concentration. Recently, Jansen et al. proposed a theory attributing increases in polymerization rate to increases in monomer dipole moment (Jansen, J. F. G. A.; Dias, A. A.; Dorschu, M.; Coussens, B. Macromolecules 2002, 35, 7529). Although such mechanisms may contribute to the reactivity and unique material properties achieved in these polymers, they do not provide a complete explanation.

This example expands on Decker's monomer systems to gain an understanding of the mechanism or mechanisms for the polymerization kinetics and ability to crosslink. The specific goal is to elucidate the relationship between monomer functionality and monomer structure in relationship to polymerization kinetics and polymer network structure. A better understanding of the mechanism(s) through which these materials polymerize will allow monomer design to be better tailored such that specific properties will be attained.

Experimental: Instrumentation

Molecular weight between crosslinks ($M_c$) was obtained from mechanical property data obtained from a Perkin-Elmer DM 7e Dynamic Mechanical Analyzer. $M_c$ was calculated from the following equation:

$$M_c = \frac{3RT\rho}{E'}$$

where R is the gas constant, ρ is the polymer density, E' is the storage modulus in the rubbery plateau, and T is the absolute temperature where the storage modulus was evaluated (Hill, L. W. Coating Tech. 1992, 64, 29).

Steady state and unsteady state kinetic data was obtained from a Nicolet Magna 760 FTIR spectrometer equipped with a horizontal transmittance apparatus. All systems were polymerized with 5 mW/cm$^2$ of ultraviolet light, using a filtered (peak irradiation wavelength: 365 nm) EXFO Ultracure 100 ss light source and 0.1 wt % 2,2-dimethoxyphenylacetophenone (DMPA) as the photoinitiator.

Results and Discussion

This work proposes and evaluates several mechanistic theories for the enhanced reactivities and material properties exhibited by these monomers. Specifically, hydrogen bonding, hydrogen abstraction, and electronic and resonance effects are explored. Each of these mechanisms is interrelated; thus, it is difficult to isolate their individual contribution to the polymerization reaction. Nonetheless, experiments can be developed to emphasize each of the above mechanisms individually to test its validity.

To examine the possibility of hydrogen abstraction, the material properties of acrylate monomers were examined with experiments designed to look specifically at the molecular weight between crosslinks. Table II summarizes these material properties and compares the properties to those of conventional acrylate polymers, which were polymerized at 25° C.

TABLE II

| Monomer | $M_c$ (g/mol) | [XL] (mol/L) |
|---|---|---|
| Benzyl Carbamate Acrylate | 40200 | 0.03 |
| Benzyl Carbonate Acrylate | 50800 | 0.02 |
| Phenyl Carbonate Acrylate | 41100 | 0.03 |
| Hydroxy Ethyl Acrylate | 12000 | 0.09 |
| Hydroxy Propyl Acrylate | 20400 | 0.05 |

The material property studies outlined above in Table II all utilized a photoinitiator (DMPA) concentration of 0.1 wt %≈4×10$^{-3}$ mol/L and a light intensity of 5 mW/cm$^2$. Hydrogen abstraction/chain transfer generates branching and from which crosslinks can be formed via termination by combination of these branches. Thus, if the proposed hydrogen abstraction/chain transfer mechanism is solely responsible for crosslink formation in these materials, one would expect the quantification of crosslinks to be, at a maximum, of the same order as that of the initiator concentration. However, these materials exhibit crosslink formation that exceeds the initiator concentration by almost 10-fold. Thus, traditional hydrogen abstraction/chain transfer, although a viable mechanism for the crosslinking ability of these monomers, cannot be the sole mechanism responsible for crosslink formation.

Figure 7:
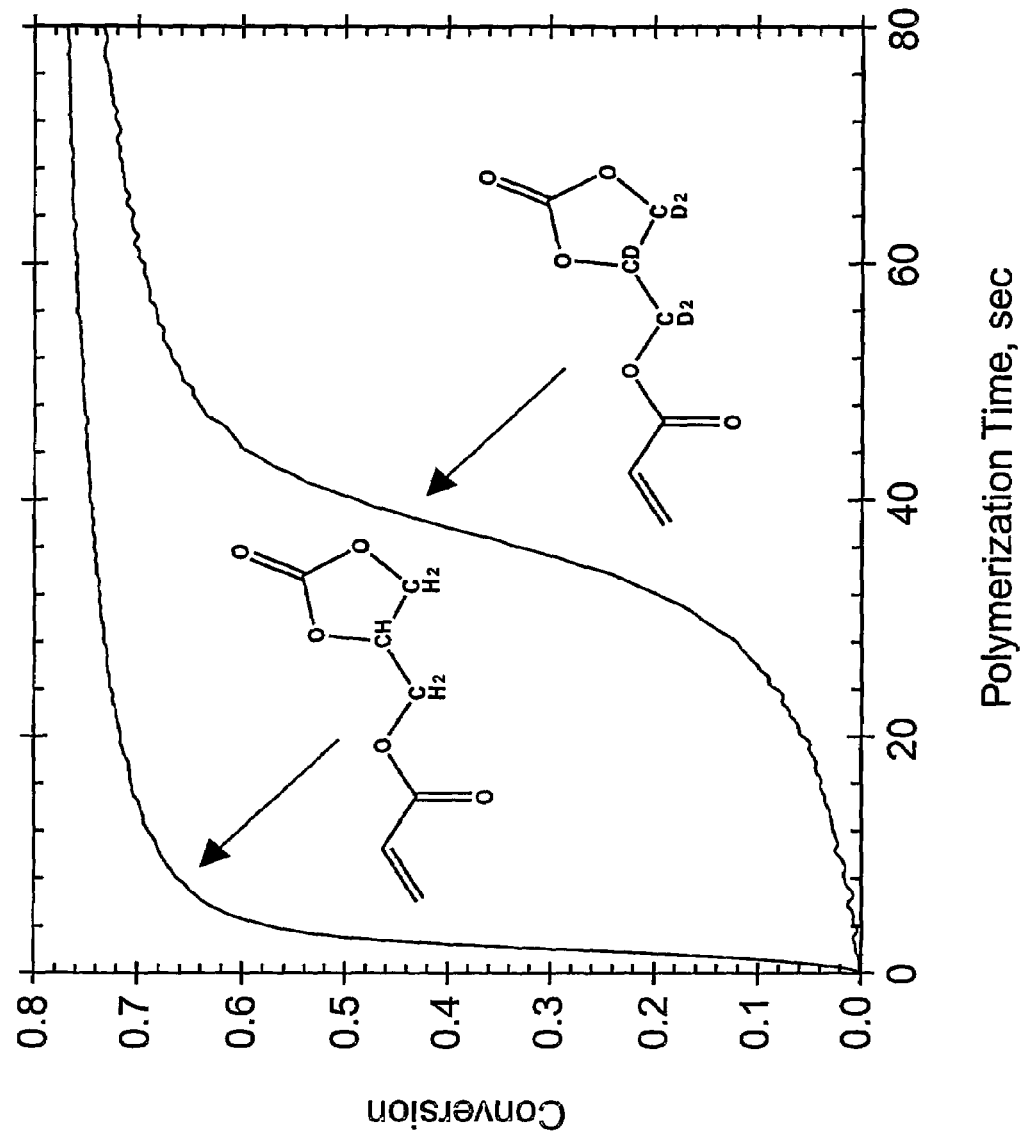
FIG. 7 is a data graph (abscissa—polymerization time (seconds); ordinate—extent of conversion) that shows the relationship between hydrogen abstraction and reactivity.

In addition, FIG. 7 is a data graph that shows the relationship between hydrogen abstraction and reactivity. In particular, the reactivity of a deuterated acrylamide versus that of the non-deuterated acrylamide is shown and indicates that hydrogen abstraction is very important to the enhanced reactivity exhibited by this system. Furthermore, FIG. 8 is a data graph that shows the impact of phenyl carbamate acrylate spacer length ($R_3$) on reactivity. More specifically, the polymerizations of phenyl carbamate ethyl acrylate (A), phenyl carbamate propyl acrylate (B), phenyl carbamate butyl acrylate (C), and phenyl carbamate ethyl acrylate (D) are shown and indicate that increasing the distance between secondary functionalities ($R_4$) and acrylic double bonds decreases the polymerization rate.

Since hydrogen abstraction cannot fully account for the crosslink concentration and polymerization kinetics of these monomers, the possibility of electronic and resonance effects on the polymerization rate of the monomers was also investigated. To accomplish the electronic and resonance studies, monomers with electron withdrawing substituents on an aromatic end group substituent were synthesized. The compound of formula III shows the arrangement of electron withdrawing substituents on an aryl end group, where $R_1$, $R_2$, and $R_3$ can be P, CN, MeO or H. As described further below, systematic variations of this phenyl carbamate acrylate were also used to characterize dipole effects of the monomer.

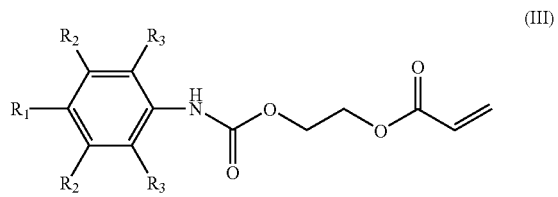

(III)

The electron withdrawing substituent studies revealed some very intriguing results. FIG. 9 shows the steady state bulk polymerizations of the electron withdrawing (fluoro-substituted) monomers. In particular, the monovinyl systems presented are: (1) unsubstituted, (2) meta, (3) ortho, (4) para, (5) penta, and (6) dimeta fluoro-substituted. From FIG. 9, it is evident that the meta substituted monomer does not have a significant polymerization rate difference from the unsubstituted monomer. However, the para, ortho, and penta substituted monomers decreased by approximately 2-fold in polymerization rate as compared to the meta and unsubstituted monomers. To determine the root cause of the polymerization rate difference in the differing monomers, unsteady state experiments were performed to deduce the kinetic constants for each monomer. FIGS. 10 and 11 show $k_p$ and $k_t$, respectively, versus conversion for the systems studied. $k_p$ is the propagation kinetic constant and $k_t$ is the termination kinetic constant and were calculated using the reaction diffusion coefficient as described in Anseth et al. *Macromolecules* 1995, 28,4040-4043. FIGS. 10 and 11 reveal that the meta substituted and unsubstituted monomers have approximately equivalent $k_p$ and $k_t$ values over the conversion range studied. However, the para, ortho, and penta substituted monomers show drastically different kinetic values as compared to the meta and unsubstituted monomers. There is an approximate 2-fold increase in $k_p$ and an approximate 10-fold increase in $k_t$ for the para, ortho, and penta substituted monomers as compared to the meta and unsubstituted monomers. Unsteady state analysis of the fluoro-substituted monomer shows a significant electronic and resonance effect on the kinetics. These electronic effects will be influenced by several factors, including the dipole moment of the molecule, as the choice of substituent and position on the benzene ring will affect the overall dipole moment of the molecule. Additionally, these benzene ring substituents will influence the degree of abstraction and chain transfer attainable from these monomers. The most significant observed effect is associated with the termination kinetics, as the para and othro substitutions significantly increase the termination of these monomers, thus decreasing the overall polymerization rate.

The fluoro-substitution results verify that the electronic and resonance effects do influence the reactivity of these monomers. The results show that a specific substituent can negatively impact the overall polymerization rate. However, with careful selection of an appropriate substituent, a positive influence is observed and the overall polymerization rate is increased.

FIG. 12 is a data graph that illustrates the propagation kinetic constant ($k_p$) versus conversion for a methoxy-substituted monomer corresponding to a compound of the formula III (described above), whereas FIG. 13 is a data graph that illustrates the termination kinetic constant ($k_t$) versus conversion for the methoxy-substituted monomer. A rate reduction due to increased termination is shown.

The relationship between dipole moment and polymerization rate was also analyzed using methods described in Jansen et al. *Macromolecules* 2002, 35, 7529-7531. See also, International Publication No. WO 02/42383, entitled "Radiation Curable Compositions," by Jansen et al, which published May 30, 2002. In particular, dipole moment calculations were performed using the equation for Boltzman weighted dipole moment, as follows:

$$<D> = \sum_j D_j \frac{e^{-\Delta E_j/RT}}{\sum_i e^{-\Delta E_i/RT}} = \sum_j D_j p_j$$

in which $\Delta E_j$ is the difference between energy of conformation j and the global minimum conformation, R is the ideal gas constant, T is absolute temperature, and $P_j$ is the probability of finding the molecule in conformation j at the temperature T. In addition, HyperChem 7.0® was utilized to perform conformational searches of the molecules. Dihedral angles were varied and the program compiled 1000 configurations based on randomization of dihedral angles. Further, low E molecules were kept while duplicate and high energy molecules were discarded. Table III shows the calculated dipole moments for various methoxy-substituted acrylates.

TABLE III

| Monomer | Caluclated Dipole Moment (Debye) | Rate Comparison |
|---|---|---|
| Phenyl Carbamate Acrylate | 2.39 | 1.0 |
| p-Methoxyphenyl Carbamate Acrylate | 1.80 | 0.6 |
| m-Methoxyphenyl Carbamate Acrylate | 3.21 | 0.6 |
| o-Methoxyphenyl Carbamate Acrylate | 3.38 | 0.6 |

The rate comparison is the substituted monomer rate/unsubstituted monomer rate (determined for average rates over X=70%). As illustrated, calculated dipole moment variations of around 1.5 Debye show an insignificant increase in polymerization rates. FIG. 14 is a data graph that graphically shows the data presented in Table III. In addition, Table IV shows the calculated dipole moments for various fluoro-substituted acrylates.

TABLE IV

| Monomer | Calculated Dipole Moment (Debye) | Rate Comparison |
|---|---|---|
| Phenyl Carbamate Acrylate | 2.39 | 1.0 |
| p-Fluorophenyl Carbamate Acrylate | 3.46 | 0.5 |
| m-Fluorophenyl Carbamate Acrylate | 2.85 | 1.0 |
| o-Fluorophenyl Carbamate Acrylate | 1.82 | 0.5 |
| Pentafluorophenyl Carbamate Acrylate | 3.65 | 0.4 |

As in Table III above, the rate comparison is the substituted monomer rate/unsubstituted monomer rate (determined for average rates over X=70%). As shown in Table IV, even about a two-fold increase in dipole moment (e.g., o-Fluorophenyl Carbamate Acrylate v. Pentafluorophenyl Carbamate Acrylate) shows little change in polymerization rate. FIG. 15 is a data graph that graphically shows the data presented in Table IV. This data indicates that there is no significant correlation between dipole moment and rate.

The effect of hydrogen bonding on reactivity was also analyzed. For example, Table V shows the effect of hydrogen bonding of methoxy-substituents.

TABLE V

| 67° C. | $V_{peak\,max}^{NH}$ Prepolymerization ($cm^{-1}$) | Time to Reach X = 70% (s) |
|---|---|---|
| Phenyl Carbamate Acrylate | 3342 | 2.3 |
| p-Methoxyphenyl Cabamate Acrylate | 3342 | 3.6 |
| m-Methoxyphenyl Carbamate Acrylate | 3342 | 3.7 |

As shown, all of these monomers show approximately equivalent hydrogen bonding, but the polymerization rates differ significantly. Table VI shows the effect of hydrogen bonding of fluoro-substituents.

TABLE VI

| 67° C. | $V_{peak\,max}^{NH}$ Prepolymerization ($cm^{-1}$) | Time to Reach X = 70% (s) |
|---|---|---|
| Phenyl Carbamate Acrylate | 3342 | 2.3 |
| p-Fluorophenyl Cabamate Acrylate | 3339 | 4.6 |
| m-Fluorophenyl Carbamate Acrylate | 3339 | 2.3 |
| o-Fluorophenyl Carbamate Acrylate | 3340 | 4.4 |
| Pentafluorophenyl Carbamate Acrylate | 3300 | 4.8 |

As shown, the strongest hydrogen bonding monomer (pentafluorophenyl carbamate acrylate) shows one of the slowest polymerization rates, whereas a weaker hydrogen bonding monomer, such as phenyl carbamate acrylate, shows the greatest rate.

CONCLUSIONS

As described herein, monovinyl (meth)acrylates have been developed that show ultrarapid polymerization and the ability to form crosslinked networks. The exact mechanism(s) for these enhanced polymer properties are not well understood. Hydrogen abstraction/chain transfer is a possible mechanism for the ability to crosslink, but this chain transfer cannot account for the significant crosslink concentrations measured in these materials. In addition, electronic and resonance effects show a significant influence on the polymerization kinetics of these polymers. Electron withdrawing substituents on the benzene ring alter the reactivities of the monomer and display a significant increase in termination kinetics for the para, ortho, and penta substitutions. Further, there is lack of significant correlation between dipole moment and polymerization rate for the monomers analyzed above. Moreover, hydrogen bonding does not appear to be a major contributor to enhanced reactivity.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above may be used in various combinations. All publications, patents, patent applications, or other documents cited in this application are incorporated by reference in their entirety for all purposes to the same extent as if each individual publication, patent, patent application, or other document were individually indicated to be incorporated by reference for all purposes.

What is claimed is:

1. A monomer selected from the following structures:

Compound 1
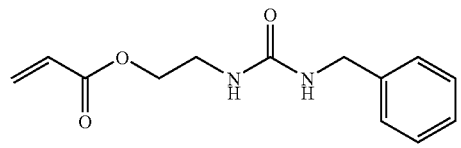

Compound 2
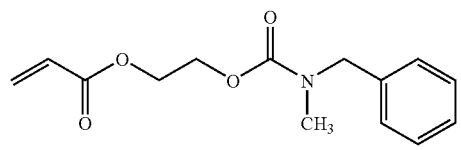

Compound 3
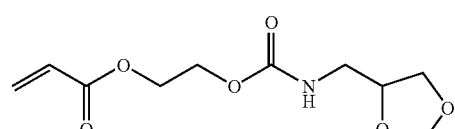

Compound 4
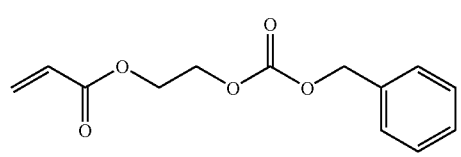

Compound 5
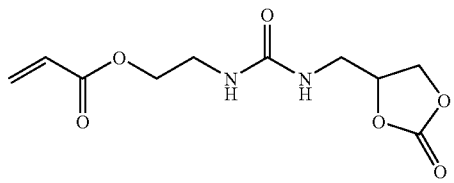

Compound 6
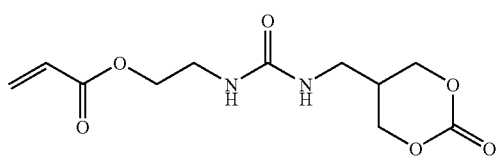

Compound 7
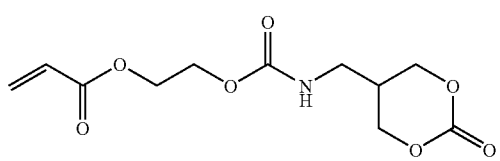

Compound 8
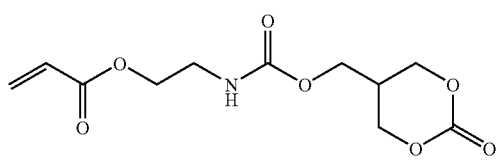

Compound 9
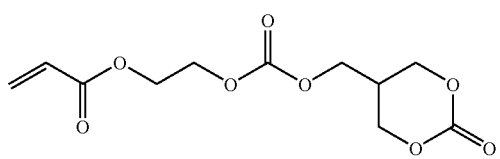

Compound 10
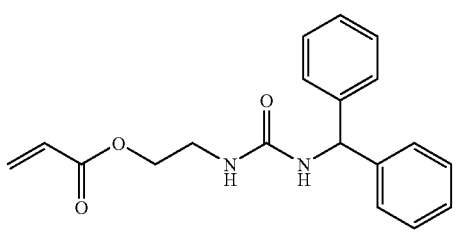

Compound 11
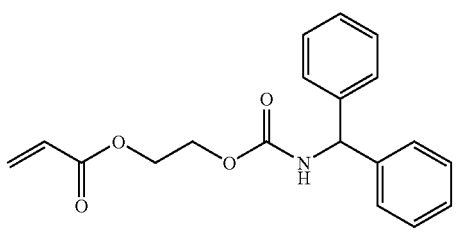

-continued
Compound 12
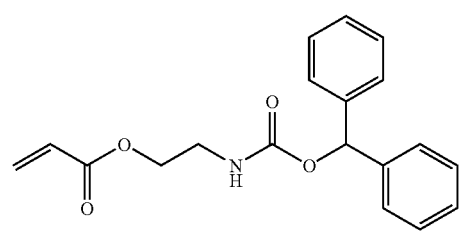
Compound 13
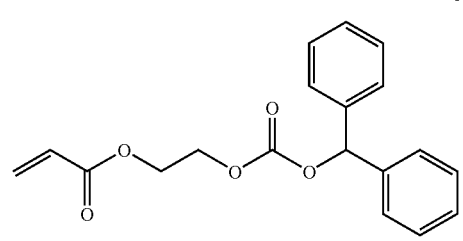
Compound 14
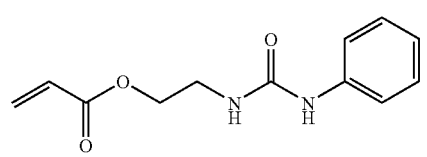
Compound 15
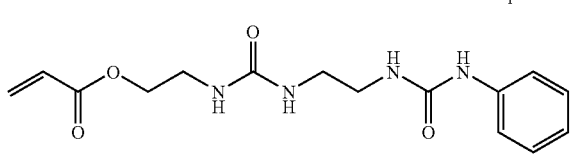
Compound 16
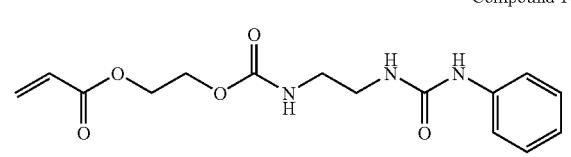
Compound 17
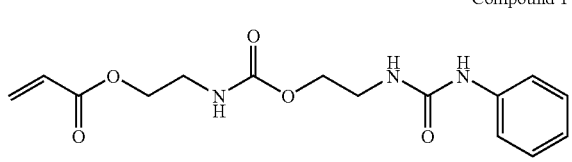
Compound 18
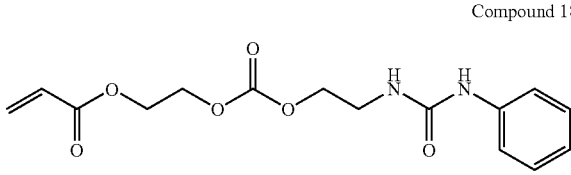
Compound 19
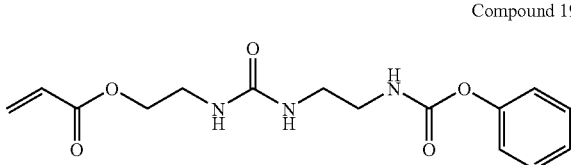
-continued
Compound 20
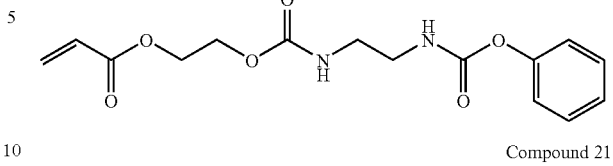
Compound 21
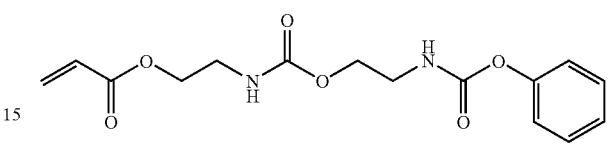
Compound 22
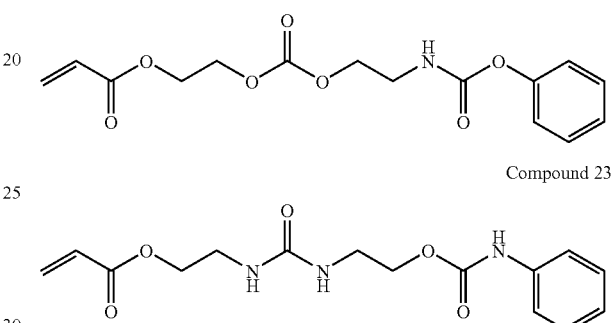
Compound 23
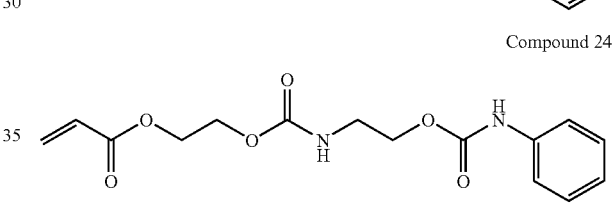
Compound 24
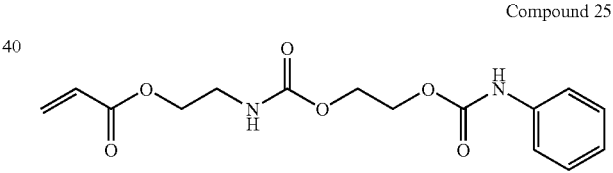
Compound 25
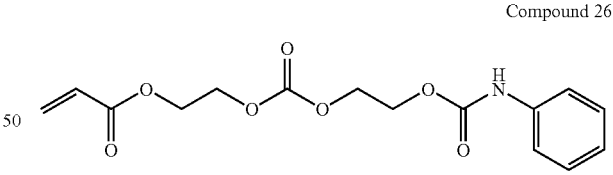
Compound 26
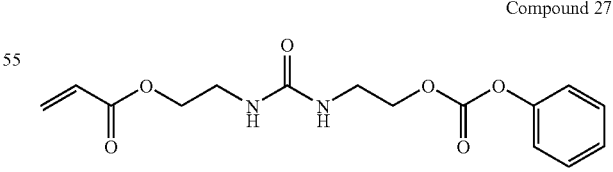
Compound 27
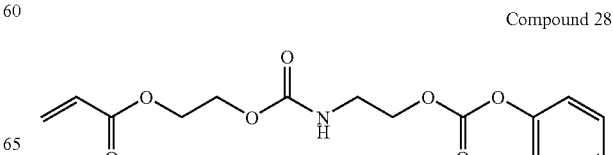
Compound 28

-continued
Compound 29
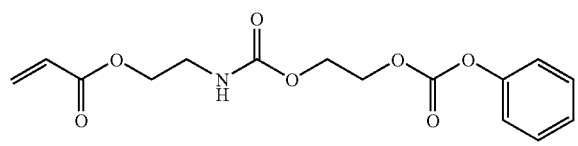
Compound 30
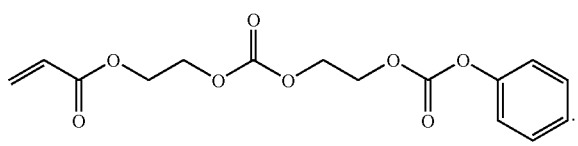
2. A method of producing a polymer, the method comprising reacting at least two monomers with one another, wherein at least one of the monomers is selected from the following structures:
Compound 1
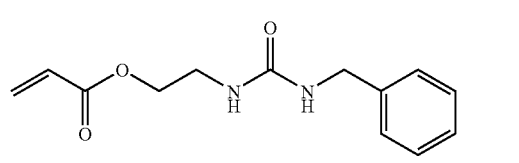
Compound 2
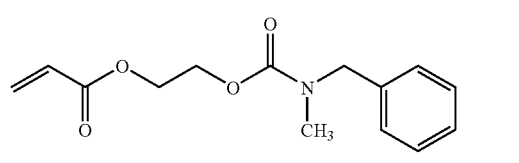
Compound 3
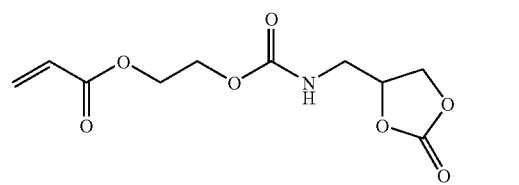
Compound 4
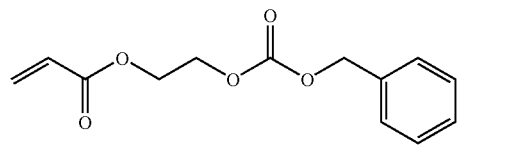
Compound 5
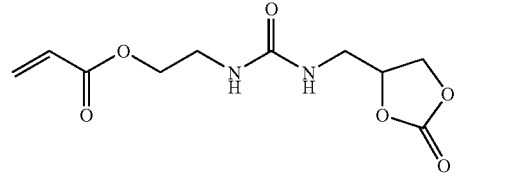
-continued
Compound 6
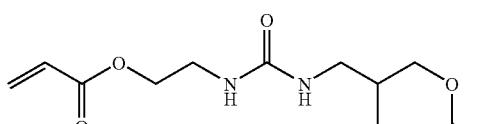
Compound 7
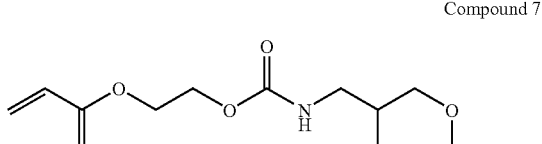
Compound 8
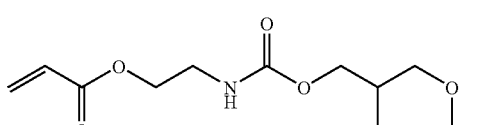
Compound 9
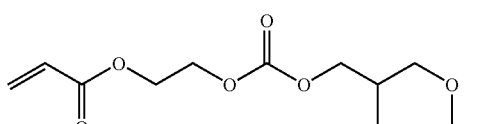
Compound 10
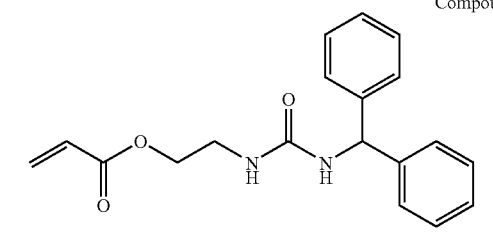
Compound 11
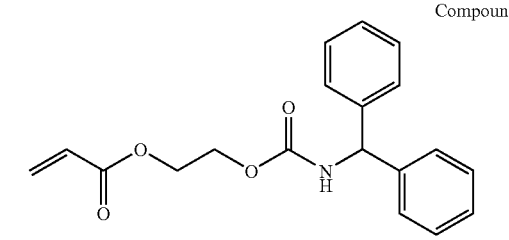
Compound 12
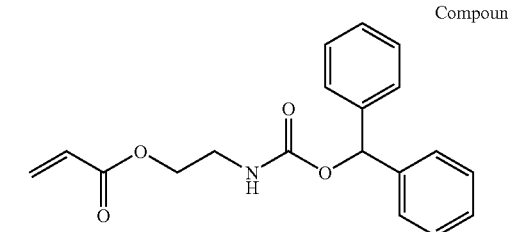

Compound 13
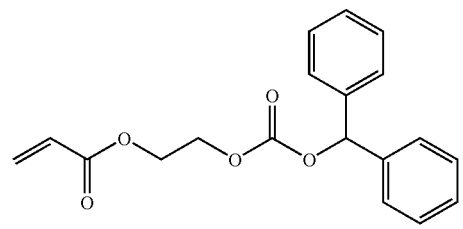
Compound 14
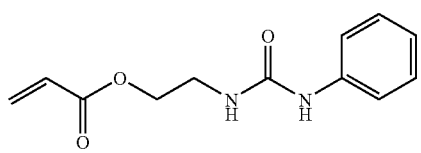
Compound 15
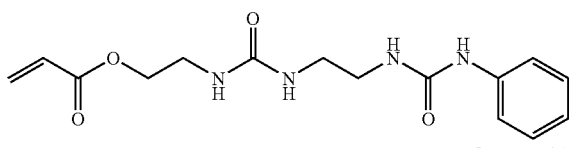
Compound 16
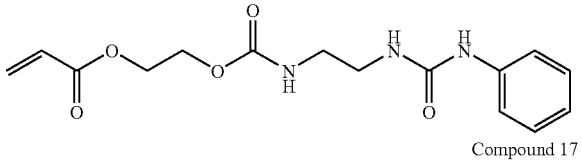
Compound 17
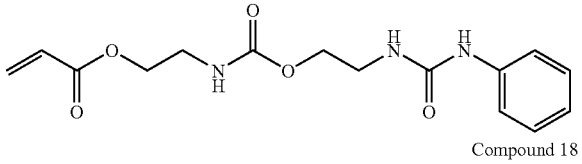
Compound 18
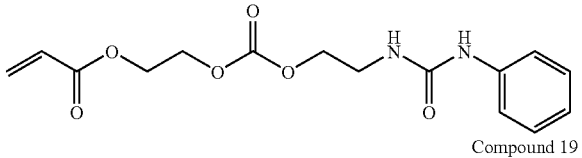
Compound 19
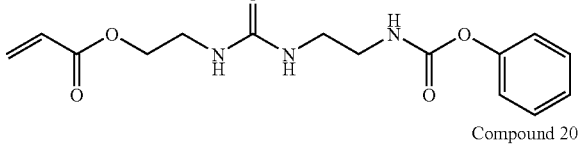
Compound 20
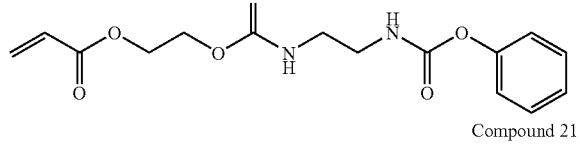
Compound 21
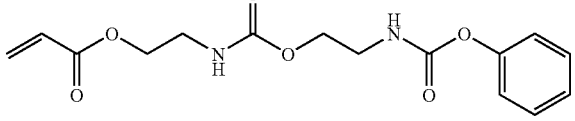
Compound 22
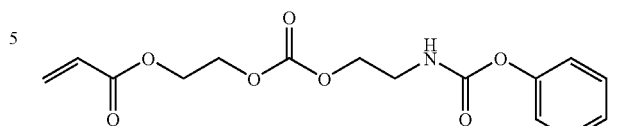
Compound 23
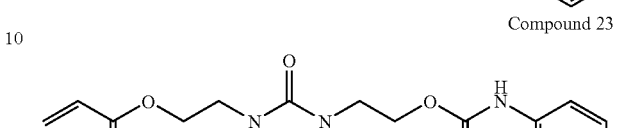
Compound 24
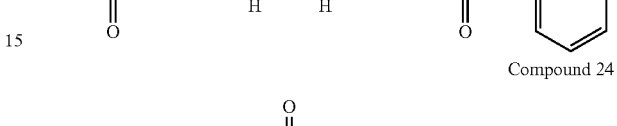
Compound 25
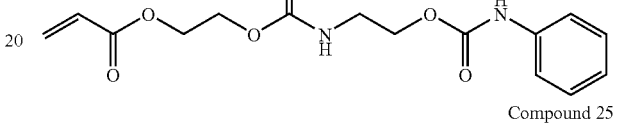
Compound 26
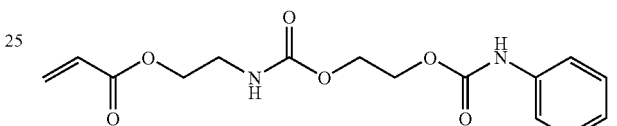
Compound 27
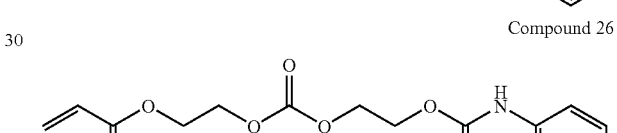
Compound 28
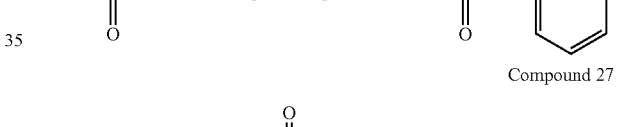
Compound 29
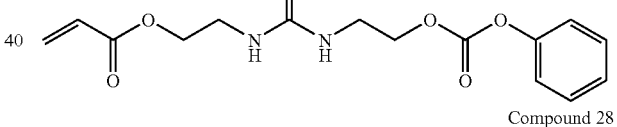
Compound 30
* * * * *